(12) United States Patent
Disis et al.

(10) Patent No.: US 8,216,789 B2
(45) Date of Patent: Jul. 10, 2012

(54) DIAGNOSTIC PANEL OF CANCER ANTIBODIES AND METHODS FOR USE

(75) Inventors: Mary L. Disis, Renton, WA (US); Vivian Goodell, San Diego, CA (US); Hailing Lu, Seattle, WA (US)

(73) Assignee: University of Washington, Seattle, WA (US)

( * ) Notice: Subject to any disclaimer, the term of this patent is extended or adjusted under 35 U.S.C. 154(b) by 294 days.

(21) Appl. No.: 12/394,922

(22) Filed: Feb. 27, 2009

(65) Prior Publication Data

US 2009/0215091 A1   Aug. 27, 2009

Related U.S. Application Data

(60) Provisional application No. 61/031,836, filed on Feb. 27, 2008, provisional application No. 61/039,163, filed on Mar. 25, 2008.

(51) Int. Cl.
*G01N 33/53* (2006.01)

(52) U.S. Cl. ........................................ 435/7.1

(58) Field of Classification Search .................. None
See application file for complete search history.

(56) References Cited

U.S. PATENT DOCUMENTS

2005/0221305 A1   10/2005   Nelson

FOREIGN PATENT DOCUMENTS

WO   WO/03/064593   8/2003
WO   WO/2004/063325   7/2004

OTHER PUBLICATIONS

Tockman et al (Cancer Res., 1992, 52:2711s-2718s).*
Konstadoulakis et al (Journal of Clinical Immunology, 1994, 14(5): 310-313).*
Sthoeger et al (Ann N Y Acad Sci, 1997, 815: 496-498).*
Zhang et al (Cancer Epidemiol Biomarkers, 2003, 12: 136-143).*
Albanoupoulos et al (Am J Gastroenterol, 2000, 95(4): 1056-1061).*
Albanopoulos, K. et al., "Prognostic significance of circulating antibodies against carcinoembryonic antigen (anti-CEA) . . . cancer", 2000, *Amer J of Gastro*, 95(4):1056-61.
Angelopoulou, K.; et al., "Prevalence of serum antibodies against the p53 tumor suppressor gene protein in various cancers", 1994, *Int. J. Cancer* 58: 480-487.
Bachelot, T.; et al., "Autoantibodies to endostatin in patients with breast cancer: correlation to endostatin levels and clinical outcome", 2006 *Br. J. Cancer* 94:1066-1070.
Baron-Hay, S., et al. "Elevated serum insulin-like growth factor binding protein-2 as a prognostic marker in patients with ovarian cancer" 2004, *Clin Cancer Res* 10:1796-1806.
Broll, R., et al., "p53 autoantibodies in sera of patients with a colorectal cancer and their association to p53 protein concentration . . . tissue", 2001, *Int J Colorectal Dis* 16(1):22-7.
Busund, L.T. et al. "Significant expression of IGFBP2 in breast cancer compared with benign lesions", 2005, *J Clin Pathol* 58:361-366.
Carter, D.; et al., "Serum antibodies to lipophilin B detected in late stage breast cancer patients", 2003 *Clin. Cancer Res.* 9:749-754.

Chapman, C.; et al., "Autoantibodies in breast cancer: their use as an aid to early diagnosis", 2007 *Ann. Oncol.* 18:868-873.
Cho-Chung, Y. S., "Autoantibody biomarkers in the detection of cancer", 2006, *Biochim. Biophys. Acta* 1762: 587-591.
Clark, R., "The Somatogenic hormones and insulin-like growth factor-1: stimulators of lymphocytes and immune function", *Endocrine Reviews*, 1997, 18(2):157-179.
Conroy, S. E. et al., "Autoantibodies to 90 kD heat-shock protein in sera of breast cancer patients", 1995, *Lancet* 345: 126.
Crawford, L. V.; et al., "Detection of antibodies against the cellular protein p53 in sera from patients with breast cancer", 1982, *Int. J. Cancer* 30: 403-408.
Dalifard, I.; et al., "Cytosolic p53 protein and serum p53 autoantibody evaluation in breast cancer. Comparison with prognostic factors", 1999 *Anticancer Res.* 19: 5015-5022.
Davidoff, A. M.; et al., "Genetic basis for p53 overexpression in human breast cancer", 1991 *Proc. Natl. Acad. Sci. U.S.A.* 88:5006-5010.
Di Modugno, F. et al., "Human Mena Protein, A serex-defined antigen overexpressed in breast cancer eliciting . . . response", 2004, *Int J Cancer* 109: 909-918.
Disis, M. L.; et al., "Existent T-cell and antibody immunity to HER-2/neu protein in patients with breast cancer", 1994, *Cancer Res.* 54: 16-20.
Disis, M. L.; et al., "High-titer HER-2/neu protein-specific antibody can be detected in patients with early-stage breast cancer", 1997*J. Clin. Oncol.* 15: 3363-3367. Disis, M. L.; et al., "Pre-existent immunity to the HER-2/neu oncogenic protein in patients with HER-2/neu overexposing . . . cancer", 2000, *Breast Cancer Res. Treat.* 62: 245-252.
Disis, M.L., et al., "Global role of the immune system in identifying cancer initiation and limiting disease progression", 2005, *J Clinical Oncology* 23:(35) 8923-8925.
Disis, M.L., et al., "Molecular targeting with cancer vaccines", 2005, *J Clinical Oncology* 23:(22) 4840-4841.
Disis, M.L., et al., Soluble cytokines can act as effective adjuvants in plasmid DNA vaccines targeting . . . antigens, 2003, *Immunobiology* 207: 1-8.
Flyvbjerg, A., et al., "Elevated Serum insulin-like growth factor-binding protein 2 (IGFBP-2) and decreased IGFBP-3 . . . inhibitor", 1997 *J Clin Endocrinol Metab.* 82(7): 2308-13.

(Continued)

*Primary Examiner* — Sean Aeder
(74) *Attorney, Agent, or Firm* — Karen S. Canady; Canady + Lortz LLP

(57) ABSTRACT

The invention provides a method for detection of a malignancy in a specimen of bodily fluid. The method comprises contacting the specimen with at least two antigens selected from the group consisting of p53, IGFBP2, Topo2α, cathepsin D, cyclin B, cyclin D1, MUC1, HER-2/neu and CEA. The method further comprises incubating the specimen and the antigen for a duration and under conditions that are sufficient for the formation of immunocomplexes; and detecting the presence or absence of immunocomplex formation between the antigens and antibodies specific for the antigens in the specimen, thereby determining the presence or absence of the malignancy. Also provided is a method for monitoring the effectiveness of cancer therapy related to a malignancy in a warm-blooded animal, a method for distinguishing between Stage I and Stage II colorectal cancer in a specimen of bodily fluid.

8 Claims, 12 Drawing Sheets

OTHER PUBLICATIONS

Foll, J.L. et al., "Activation-dependent expression of the insulin-like growth factor binding protein-2 in human lymphocytes", *Immunology*, 1998, 94:173-180.

Fottner, Ch. et al., "Role of the insulin-like growth factor system in adrenocortical growth control and carcinogenesis", 2004, *Horm Metab Res* 36: 397-405.

Gao, R. J.; et al., "The presence of serum anti-p53 antibodies from patients with invasive ductal carcinoma of breast: parameters", 2005, *Breast Cancer Res. Treat.* 93: 111-115.

Gnjatic, S., et al., "Survey of naturally occurring CD4+ T cell responses against NY-ESO-1 in cancer patients: correlation . . . responses", 2003, *Proc Natl Acad Sci* 100(15):8862-8867.

Goodell, V.; Disis, M. L., "Human tumor cell lysates as a protein source for the detection of cancer antigen-specific humoral immunity" 2005 *J. Immunol. Methods* 299:129-138.

Goodell, V.; et al., "Antibody immunity to the p53 oncogenic protein is a prognostic indicator in ovarian cancer", *J. Clin. Oncol.* 2006 24:762-768.

Green, J. A.; et al., "Serum p53 auto-antibodies: incidence in familial breast cancer", *Eur. J. Cancer* 1994 30A 580-584.

Hoeflich, A. et al., "Insulin-like growth factor-binding protein 2 in tumorigenesis: protector or promoter?", 2001, *Cancer Res*. 61: 8601-10.

Jager, D., et al. "Identification of tumor antigens as potential target antigens for immunotherapy by serological . . . cloning", 2004, *Cancer Immunol Immunother* 53:144-147.

Kanety, H. et al., "Increased insulin-like growth factor binding protein-2 (IGFBP-2) gene expression and protein production . . . fluid", 1996, *Br J Cancer* 73: 1069-73.

Karasik, A. et al., "Insulin-like growth factor-I (IGF-I) and IGF-binding protein-2 are increased in cyst fluids of epithelial . . . cancer", 1994,*J Clin Endocrinol Metab*. 78: 271-6.

Kawamoto, K. et al., "Expression of Insulin-like growth factor-2 can predict the prognosis of human colorectal cancer patients . . . survival", 1998, *Oncology*. 55: 242-8.

Kotera, Y.; et al., "Humoral immunity against a tandem repeat epitope of human mucin MUC-1 in sera from breast, pancreatic . . . patients", 1994 *Cancer Res*. 54:2856-2860.

Lechpammer, M.; et al., "Humoral immune respone to p53 correlates with clinical course in colorectal cancer patients . . . chemotherapy", 2004, *Int. J. Colorectal Dis*. 19: 114-120.

Lee, E.-J., et al., "Insulin-like growth factor binding protein 2 promotes ovarian cancer cell invasion", 2005, *Molecular Cancer* 4:7.

Lu, H., et al., "Serum antibodies specific for tumor antigens in colorectal . . . biomarkers", 2006, *J Clinical Oncology ASCO Mtg Proceed Part 1*, 24(18S): Abstract No. 10041.

Martin, J.L. et al., "Expression of insulin-like growth factor binding protein-2 by MCF-7 breast cancer cells is regulated through . . . Pathway", 2007, *Endocrinology* 148:2532-2541.

Mehrian-Shai, R. et al. "Insulin growth factor-binding protein 2 is a candidate biomarker for PTEN status and P13K/Akt . . . cancer", 2007, *Proc Natl Acad Sci USA* 104(13):5563-5568.

Miraki-Moud, F., et al., "Increased levels of insulin-like growth factor binding protein-2 in sera and tumors from patients . . . acromegaly", 2001, *Clin Endocrinol (Oxf)*. 54: 499-508.

Mita, K., et al., "Expression of the insulin-like growth factor system and cancer progression in hormone-treated prostate cancer patients", 2000, *Int J Urol*. 7: 321-9.

Mudenda, B.; et al., "the relationship between serum p53 autoantibodies and characteristics of human breast cancer", 1994, *Br. J. Cancer*69: 1115-1119.

Muller, M.; et al., "Testing for anti-p53 antibodies increases the diagnostic sensitivity of conventional tumor markers", 2006 *Int. J. Oncol* 29:973-980.

Nakatsura, T., et al., "Cellular and humoral immune responses to a human pancreatic cancer antigen, coactosin-like protein . . . method", 2002. *Eur J Immunol* 32:826-836.

Perks, C.M., et al., "IGF-II and IGFBP-2 differentially regulate PTEN in human breast cancer cells", 2007, *Oncogenel* 26(40):5966-572.

Peyrat, J. P.; et al., "Prognostic significance of circulating p53 antibodies in patients undergoing surgery for locoregional breast cancer", 1995, *Lancet* 345: 621-622.

Pollak, M.N. et al., "Insulin-like growth factors and neoplasia", 2004, *Nat Rev Cancer* 4:505-518.

Pupa, S. M. et al., "Letters to the Editor: Humoral immune response for early diagnosis of breast carcinoma", 2002, *Ann. Oncol*. 13: 483.

Regele, S.; et al., "p53 autoantibodies can be indicative of the development of breast cancer relapse", 2003, *Anticancer Res*. 23: 761-764.

Regidor, P. A.; et al., "Detection of p53 auto-antibodies in the sera of breast cancer patients with a new recurrence . . . exist?", 1996, *Eur. J. Gynaecol. Oncol.* 17: 192-199.

Renehan, A.G. et al. "Elevated serum insulin-like growth factor (IGF)-II and IGF binding protein-2 in patients with colorectal cancer", 2000, *Br J Cancer* 83(10):1344-1350.

Salazar, L. et al., "Cancer Vaccines: the role of tumor burden in tipping the scale toward vaccine efficacy", 2005, *J Clinical Oncology* 23(30):7397-7398.

Schutt, B.S., et al., "Integrin-mediated action of insulin-like growth factor binding protein-2 in tumor cells", 2004, *J Mol Endocrinol* 32:859-868.

Shariat, S. F. et al. "Association of preoperative plasma levels of insulin-like growth factor I and insulin-like growth factor binding . . . metastasis", 2002, *J Clin Oncol*. 20:833-41.

Stattin, P., et al., "Plasma Insulin-like growth factor-I, insulin-like growth factor-binding proteins, and prostate cancer . . . study", 2000, *J Natl Cancer Inst*. 92: 1910-7.

Suzuki, H. et al., "T cell-dependent antibody responses against aberrantly expressed cyclin B1 protein in patients with cancer . . . disease", 2005 *Clin. Cancer Res*. 11:1521-1526.

Takeda, A., et al., "Serum p53 antibody as a useful marker for monitoring of treatment of superficial colorectal adenocarcinoma after . . . resection", 2001, *Int J Clin Oncol* 6:45-49.

Thompson, J. et al., "Tumor cells transduced with the MHC class II transactivator and CD80 activate . . . chain", 2006, *Cancer Res* 66:(2) 1147-1154.

Von Mensdorff-Pouilly, S.; et al., Humoral immune response to polymorphic epithelial mucin (MUC-1) in patients . . . tumours, 1996, *Eur. J. Cancer* 32A:1325-1331.

Wang, H., et al., "Insullin-like growth factor-binding protein 2 and 5 are differentially regulated in ovarian cancer of different histologic types", 2006, *Modern Pathology* 1-8.

Wang, X.; et al., "Autoantibody signatures in prostate cancer", 2005 *N. Engl. J. Med*. 353:1224-1235.

Willsher, P. C.; et al., "The significance of p53 autoantibodies in the serum of patients with breast cancer", 1996, *Anticancer Res*. 16: 927-930.

Yu, H., et al. "Levels of insulin-like growth factor I (IGF-I) and IGF binding proteins 2 and 3 in serial postoperative serum samples . . . recurrence", 2001, *Urology* 57:471-475.

\* cited by examiner

DIAGNOSTIC PANEL OF CANCER ANTIBODIES AND METHODS FOR USE

This application claims the benefit of U.S. provisional patent application Nos. 61/031,836, filed Feb. 27, 2008, and 61/039,163, filed Mar. 25, 2008, the entire contents of each of which are incorporated herein by reference

STATEMENT REGARDING FEDERALLY SPONSORED RESEARCH

The invention disclosed herein was made with U.S. government support under Grant Nos. K24CA85218. P30CA015704 and U54CA090818, awarded by the National Institutes of Health. The U.S. government has certain rights in this invention.

TECHNICAL FIELD OF THE INVENTION

The present invention relates generally to detection, diagnosis, and monitoring of cancer. The invention more specifically pertains to an epithelial cancer antibody panel for diagnosis and prognosis of breast, ovarian, and colon cancer. The molecules of the invention can be used in diagnostic kits and in methods of detecting, assessing and/or monitoring the malignancy of such cancers.

BACKGROUND OF THE INVENTION

Breast cancer is immunogenic and multiple tumor antigens have been identified using serum from breast cancer patients. The immunogenicity of breast cancer may be potentially utilized for the detection of the disease. Likewise, there is also evidence that ovarian cancer is immunogenic. Colorectal cancer (CRC) is the second leading cause of cancer-related death in the United States, striking 140,000 people annually and causing 60,000 deaths. Although the use of endoscopic screening is increasing, overall compliance in undergoing the procedure is poor. It is critical to develop a non-invasive test for the early detection of CRC.

There is a need to identify serum antibodies to tumor associated antigens that can be detected in cancer patients and may be used as biomarkers for cancer diagnosis.

SUMMARY OF THE INVENTION

The invention described herein is based on the discovery that antibody immunity to a panel of tumor antigens can be detected at increased levels in the sera of cancer patients, including breast, ovarian and colorectal cancer patients. The invention provides a method for detection of a malignancy in a specimen of bodily fluid. In one embodiment, the method comprises contacting the specimen with at least two antigens selected from the group consisting of p53, IGFBP2, Topo2α, cathepsin D, cyclin B, cyclin D1, MUC1, HER-2/neu and CEA. In some embodiments, the specimen is contacted with at least 3, 4, 5, 6 or 7 or more of these antigens. The method further comprises incubating the specimen and the antigen for a duration and under conditions that are sufficient for the formation of immunocomplexes; and detecting the presence or absence of immunocomplex formation between the antigens and antibodies specific for the antigens in the specimen, thereby determining the presence or absence of the malignancy.

For example, by using a combination of four antigens, insulin-like growth factor binding protein 2 (IGFBP2), p53, topoisomerase II alpha (TOPO2α), and CEA, one can discriminate serum samples from CRC patients and normal donors with 91% accuracy. The assay, using a panel of antigens is ELISA based and has been developed to meet Clinical Laboratory Improvement Act requirements. The assay has undergone both Phase I and II testing. Additional data suggests it may be useful for other GI cancers such as pancreatic cancer.

More specifically, the invention provides a method for detection of a malignancy in a specimen of bodily fluid. In a typical embodiment, the method comprises contacting the specimen with at least two antigens selected from the group consisting of p53, IGFBP2, Topo2α, cathepsin D, cyclin B, cyclin D1, MUC1, HER-2/neu and CEA. The method further comprises incubating the specimen and the antigen for a duration and under conditions that are sufficient for the formation of immunocomplexes; and detecting the presence or absence of immunocomplex formation between the antigens and antibodies specific for the antigens in the specimen, thereby determining the presence or absence of the malignancy. In one embodiment, the at least two antigens comprise cathepsin D, optionally in combination with p53. In another embodiment, the at least two antigens comprise IGFBP2, Topo2α, CEA and p53. In another embodiment, the at least two antigens comprise IGFBP2, Topo2α, HER-2/neu and p53. In one embodiment, the contacting comprises contacting the specimen with cathepsin D, IGFBP2, cyclin B, p53, Topo2α and CEA. In another embodiment, the contacting comprises contacting the specimen with p53, HER-2/neu, IGFBP2, Topo2α, MUC1, cathepsin D and cyclin D1. In another embodiment, the contacting comprises contacting the specimen with p53, HER-2/neu, CEA and cyclin B. The malignancy is can be associated with any of a variety of cancers, including epithelial cancers such as colorectal cancer, ovarian cancer, breast cancer or pancreatic cancer.

Also provided is a method for monitoring the effectiveness of cancer therapy related to a malignancy in a warm-blooded animal. The method typically comprises contacting a specimen of bodily fluid obtained from the warm-blooded animal with at least two antigens selected from the group consisting of cathepsin D, IGFBP2, cyclin B, p53, Topo2α and CEA. In an alternative embodiment, the at least two antigens are selected from the group consisting of p53, HER-2/neu, IGFBP2, Topo2α, MUC1, cathepsin D and cyclin D1. The method further comprises incubating the specimen and the antigen for a duration and under conditions that are sufficient for the formation of immunocomplexes; and detecting the presence or absence of immunocomplex formation between the antigens and antibodies specific for the antigens in the specimen, thereby determining the presence or absence of the malignancy. The absence or reduction of malignancy is indicative of effectiveness of cancer therapy. In one embodiment, the preceding steps are repeated following an administration of cancer therapy, and effectiveness of the cancer therapy is determined by comparing results of the detecting of performed before and after the administration of cancer therapy.

In a typical embodiment, the malignancy is associated with colorectal, breast, ovarian or pancreatic cancer. Other cancers are contemplated and likely to be detected by the method of the invention.

The invention additionally provides a method for distinguishing between Stage I and Stage II cancer in a specimen of bodily fluid. The method can comprise contacting the specimen with at least two antigens selected from the group consisting of cathepsin D, IGFBP2, cyclin B, p53, Topo2α and CEA; incubating the specimen and the antigen for a duration and under conditions that are sufficient for the formation of immunocomplexes; and detecting the presence or absence of immunocomplex formation between the antigens and antibodies specific for the antigens in the specimen, thereby determining the presence or absence of the malignancy. The presence of immunocomplex formation is indicative of Stage II cancer. Typically, the cancer is colorectal cancer.

The invention is further based on the discovery that cathepsin D can be used to detect cancer, such as colorectal cancer or breast. Cathepsin D can be used as a marker for detection of cancer alone, or as part of a panel of tumor antigens.

In addition, the invention provides a method for identifying a candidate subject for an aggressive treatment plan, as well as identifying a candidate subject for a moderately aggressive treatment plan or a less aggressive treatment plan. In one embodiment, the method is for determining whether to treat a cancer patient with an aggressive protocol or with modified protocol. The method comprises contacting a specimen obtained from a subject with at least two antigens described herein. The method further comprises incubating the specimen and the antigen for a duration and under conditions that are sufficient for the formation of immunocomplexes; and detecting the presence or absence of immunocomplex formation between the antigens and antibodies specific for the antigens in the specimen, thereby determining the subject's candidacy for aggressive, moderately aggressive or less aggressive treatment. In one embodiment, the subject has or is suspected of having ovarian cancer, and the antigens are p53, HER2, and TOPO2α. The aggressive protocol for ovarian cancer comprises surgery and chemotherapy and, optionally, radiation therapy. The modified protocol comprises surgery without chemotherapy. Detecting immunocomplexes with none of the three antigens, p53, HER2, and TOPO2α, in specimen from an ovarian cancer patient is indicative of a candidate for aggressive treatment, as these patients have the least favorable prognosis. Detecting immunocomplexes for at least two of these antigens in a specimen is indicative of a candidate for less aggressive treatment via the modified protocol.

DETAILED DESCRIPTION OF THE INVENTION

Figure 1A:
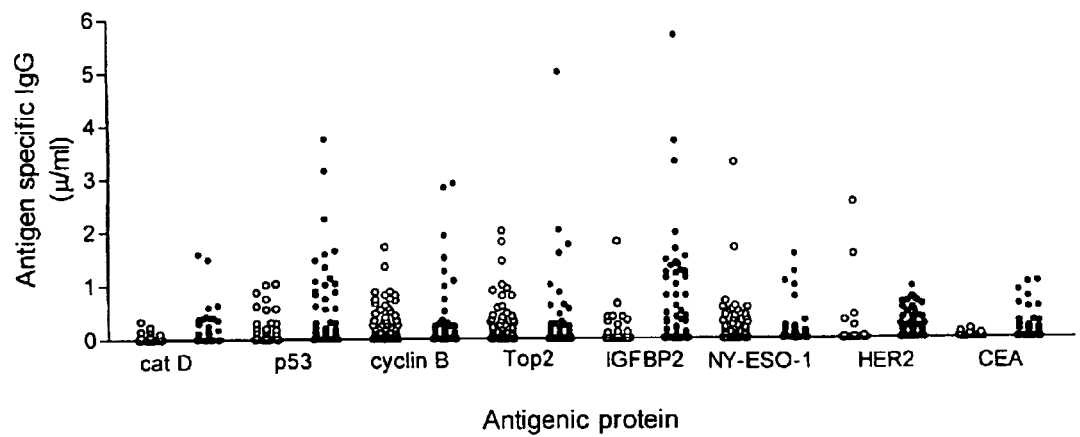
FIGS. 1A-1B. Magnitude and presence of antibodies to tumor associated antigens are higher in patients with colorectal cancer than in normal donor controls. (1A) Antibody responses to antigenic proteins are shown for 30 colorectal cancer patients (filled circles) and 100 normal donor controls (clear circles). (1B) Percent of subjects with positive antibody responses to antigenic proteins are shown for 30 colorectal cancer patients and 100 normal donor controls (clear bars).

The invention described herein is based on the discovery that antibody immunity to a panel of tumor antigens can be detected at increased levels in the sera of cancer patients, including breast, ovarian and colorectal cancer patients. Detection of these antibodies in patient specimens can be used to detect, diagnose and monitor cancer, as well as to guide in the prognosis and selection of treatment.

Definitions

All scientific and technical terms used in this application have meanings commonly used in the art unless otherwise specified. As used in this application, the following words or phrases have the meanings specified.

As used herein, "antibody" or "antibodies" includes whole or fragmented antibodies in unpurified or partially purified form (i.e., hybridoma supernatant, ascites, polyclonal antisera) or in purified form. A "purified" antibody is one that is separated from at least about 50% of the proteins with which it is initially found (i.e., as part of a hybridoma supernatant or ascites preparation). Preferably, a purified antibody is separated from at least about 60%, 75%, 90%, or 95% of the proteins with which it is initially found. Suitable derivatives may include fragments (i.e., Fab, Fab2 or single chain antibodies (Fv for example)), as are known in the art. The antibodies may be of any suitable origin or form including, for example, murine (i.e., produced by murine hybridoma cells), or expressed as humanized antibodies, chimeric antibodies, human antibodies, and the like.

As used herein, "specific" binding refers to antibody binding to a predetermined antigen. Typically, the antibody binds with an equilibrium constant, KD, corresponding to about $1 \times 10^{-7}$ M or less, and binds to the predetermined antigen with an affinity corresponding to a KD that is at least two orders of magnitude lower than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody that binds specifically to an antigen".

As used herein, the term "kd" ($sec^{-1}$), as used herein, is intended to refer to the dissociation rate constant of a particular antibody-antigen interaction.

The term "ka" ($M \times sec^{-1}$), as used herein, is intended to refer to the association rate constant of a particular antibody-antigen interaction.

The term "KD" (M), as used herein, is intended to refer to the equilibrium constant of a particular antibody-antigen interaction and is obtained by dividing the kd by the ka.

As used herein, "bodily fluids" include sera and ascites fluid.

As used herein, the term "subject" or "warm-blooded animal" includes any human or non-human animal. The term "non-human animal" includes all vertebrates, e.g., mammals and non-mammals, such as non-human primates, sheep, dog, cow, chickens, amphibians, reptiles, etc.

As used herein, "a" or "an" means at least one, unless clearly indicated otherwise.

Diagnostic Methods

The antibodies described herein may be utilized to detect cancer within a biological sample. For instance, the antibodies may be used in assays such as, for example, flow cytometric analysis, ELISA, immunoblotting (i.e., western blot), in situ detection, immunocytochemistry, and/or immunohistochemistry. Methods of carrying out such assays are well-known in the art.

The invention provides methods for detecting p53, HER-2, MUC1, IGFBP2, (TOPO2α), cyclin D1, and/or cathepsin D specific IgG immunity (i.e., production of antibodies by activated B cells having specificity for p53, HER-2, MUC1, IGFBP2, (TOPO2α), cyclin D1, and/or cathepsin D), to be used as a clinical marker for malignancies associated with over-expression of these tumor associated antigens. The detection of such autologous antibodies (i.e., auto-antibodies) raised endogenously against clinically relevant, tumor-associated proteins are useful in the development of sensitive diagnostic assays or tests. Serologic methods of analysis, by specifically focusing on IgG antibody immunity, could offer tremendous advantages by: (1) permitting rapid and high through-put screening of large numbers of sera to determine incidence of immunity; and (2) biasing antigen identification such that proteins most likely to elicit cell-mediated immunity are selected. A serologic screening method could be utilized to determine whether such immunity is detectable in patients suspected with any type of cancer involving over-expression of these antigens, which includes breast cancer. The assessment of antibody immunity is quite different from taking direct measurement of the protein level itself, in that antibody immunity could be used: (1) to indicate exposure to a tumor-associated protein (i.e., the existence of immunogenic protein); and (2) to achieve higher sensitivity levels for the detection of small amounts of the immunogenic protein.

Those skilled in the art will appreciate additional variations suitable for the method of detecting cancer in tissue through detection of a tumor associated molecule in a specimen. This method can also be used to monitor levels of these antigens in tissue of a patient undergoing treatment for cancer. The suitability of a therapeutic regimen for initial or continued treatment can be determined by monitoring antigen levels using this method.

One embodiment of the present invention relates to methods for the detection of malignancies associated with the over-expression of p53, HER-2, MUC1, IGFBP2, (TOPO2α), cyclin D1, and/or cathepsin D and related proteins, in a warm-blooded animal. These methods may be used on a one time basis when a malignancy is suspected or on a periodic basis (e.g., to monitor an individual with an elevated risk of acquiring or reacquiring a malignancy). Antibodies specific (i.e., exhibiting a binding affinity of about $10^7$ liters/mole or better) for tumor associated protein could be found in a variety of bodily fluids including sera and ascites fluid. Bodily fluids that are suspected of containing antibodies specific for the protein are combined with the protein, and incubated for a duration and under conditions that are sufficient for the formation of immunocomplexes (e.g., 4° C. for 24-48 hrs). Following the incubation, the reaction mixture is tested for the presence of immunocomplexes. Detection of one or more immunocomplexes formed between the tumor associated protein and antibodies specific for the protein may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh, 1970); the "western blot" method of Gordon et al. (U.S. Pat. No. 4,452,901); immunoprecipitation of labeled ligand (Brown et al., J. Biol. Chem. 255:4980-4983, 1980); enzyme-linked immunosorbent assays as described by, for example, Raines and Ross (J. Biol. Chem. 2575 154-5160, 1982); immunocytochemical techniques, including the use of fluorochromes (Brooks et al., Clin. Exp. Immunol. 39:477, 1980); and neutralization of activity [Bowen-Pope et al., Proc. Natl. Acad. Sci. USA 81:2396-2400 (1984)], all of which are hereby incorporated by reference. In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876, all of which are herein incorporated by reference.

For detection purposes, the tumor associated protein ("antigen") may either be labeled or unlabeled. When unlabeled, the antigen could be used in agglutination assays. In addition, unlabeled antigen could be used in combination with labeled molecules that are reactive with immunocomplexes, or in combination with labeled antibodies (second antibodies) that are reactive with the antibody directed against the protein. Alternatively, the antigen could be directly labeled with reporter groups such as radioisotopes, fluorophores, enzymes, luminescers, or dye particles. These and other labels are well known in the art and are described, for example, in the following U.S. Pat. Nos. 3,766,162; 3,791,932; 3,817,837; 3,996,345; and 4,233,402. Typically in an ELISA assay, the reporter group could be chosen from a variety of enzymes, including horseradish peroxidase, beta-galactosidase, alkaline phosphatase, and glucose oxidase.

In one embodiment, a reporter group is bound to the tumor associated protein. The step of detecting immunocomplexes involves removing substantially any unbound protein and then detecting the presence or absence of the reporter group. In another embodiment, a reporter group is bound to a second antibody capable of binding to the antibodies specific for the protein. The detection of immunocomplex formation involves the steps: (a) removing substantially any unbound antibody; (b) adding the second antibody; (c) removing substantially any unbound second antibody; and then (d) detecting the presence or absence of the reporter group. Where the antibody specific for tumor associated protein is derived from a human, the second antibody is an anti-human antibody.

In another embodiment for detecting immunocomplexes, a reporter group is bound to a molecule capable of binding to the immunocomplexes. The detection involves the steps: (a) adding the molecule, (b) removing substantially any unbound molecule, and then (c) detecting the presence or absence of the reporter group. An example of a molecule capable of binding to the immunocomplexes is protein A. It will be evident to one skilled in the art that a variety of methods for detecting the immunocomplexes could be employed within the present invention. Reporter groups suitable for use in these methods include radioisotopes, fluorophores, enzymes, luminescers, and dye particles.

In one embodiment, prior exposure of a warm-blooded animal such as humans to the tumor associated protein could be detected by testing for the presence or absence of specific activation of CD4+ or CD8+ T cells. More specifically, T cells isolated from an individual by routine techniques (e.g., Ficoll/Hypaque density gradient centrifugation of peripheral blood lymphocytes) could be incubated with the tumor associated protein. For example, T cells may be incubated in vitro for 2-9 days (typically 4 days) at 37° C. with tumor associated protein (typically, 5 μg/ml of whole protein or 25 μg/ml of an appropriate peptide or graded numbers of cells synthesizing the protein). It may be desirable to incubate another aliquot of a T cell sample in the absence of the tumor associated protein to serve as a control.

Specific activation of CD4+ or CD8+ T cells could be detected in a variety of ways. Methods for detecting specific T cell activation include detecting the proliferation of T cells, the production of cytokines (e.g., lymphokines), or the generation of cytolytic activity (i.e., generation of cytotoxic T cells specific for the protein). For CD4+ T cells, a preferred method for detecting specific T cell activation is the detection of the proliferation of T cells. For CD8+ T cells, a preferred method for detecting specific T cell activation is the detection of the generation of cytolytic activity.

Detection of the proliferation of T cells may be accomplished by a variety of known techniques. For example, T cell proliferations could be detected by measuring the rate of DNA synthesis. T cells that have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated could be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) could be measured or the relative number of T cells that are able to respond to native protein or peptides thereof, could be sufficient.
Prognostic Methods As described in Example 4 below, the number of markers present in a given patient can provide a prognostic indicator to guide treatment strategy. Median overall survival time for ovarian cancer subjects without antibodies to p53, HER2, or TOPO2α was 24 months. Subjects positive for any one of the 3 markers studied had an increase in median overall survival from 24 to 38 months, and subjects positive for any 2 antibodies studied had an increase in overall survival from 38 to 42 months. Accordingly, one can use information about the number of indicators present in a subject to assist in selecting an appropriate treatment protocol. A subject testing positive for p53, HER2 and TOPO2α, for example, could be administered a less aggressive treatment plan, while a patient testing positive for only one of these three markers would be eligible for a moderately aggressive treatment plan. Those negative for all three markers would be considered at greater risk and eligible for a more aggressive treatment plan.

For example, rather than treating all ovarian cancer patients with both surgery and chemotherapy, as is a common practice due to the absence of a test to identify patients less likely to relapse, those patients eligible for a less aggressive treatment might receive only surgery. Chemotherapy would be added for those patients testing positive for only one or none of the three identified markers. Likewise, the method described above for distinguishing between Stage I and Stage II colorectal cancer can be used to guide selection of an appropriate treatment plan for patients having colorectal cancer.

Accordingly, the invention provides a method for identifying a candidate subject for an aggressive cancer treatment plan, as well as identifying a candidate subject for a moderately aggressive treatment plan or a less aggressive treatment plan. In one embodiment, the method is for determining whether to treat a cancer patient with an aggressive protocol or with modified protocol. The method comprises contacting a specimen obtained from a subject with at least two antigens described herein. The method further comprises incubating the specimen and the antigen for a duration and under conditions that are sufficient for the formation of immunocomplexes; and detecting the presence or absence of immunocomplex formation between the antigens and antibodies specific for the antigens in the specimen, thereby determining the subject's candidacy for aggressive, moderately aggressive or less aggressive treatment. In one embodiment, the subject has or is suspected of having ovarian cancer, and the antigens are p53, HER2, and TOPO2α. The aggressive protocol for ovarian cancer comprises surgery and chemotherapy and, optionally, radiation therapy. The modified protocol comprises surgery without chemotherapy. Detecting immunocomplexes with none of the three antigens, p53, HER2, and TOPO2α, in specimen from an ovarian cancer patient is indicative of a candidate for aggressive treatment, as these patients have the least favorable prognosis. Detecting immunocomplexes for at least two of these antigens in a specimen is indicative of a candidate for less aggressive treatment via the modified protocol.
Kits For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. The antibodies of the kit may be provided in any suitable form, including frozen, lyophilized, or in a pharmaceutically acceptable buffer such as TBS or PBS. The kit may also include other reagents required for utilization of the antibodies in vitro or in vivo such as buffers (i.e., TBS, PBS), blocking agents (solutions including nonfat dry milk, normal sera, Tween-20 Detergent, BSA, or casein), and/or detection reagents (i.e., goat anti-mouse IgG biotin, streptavidin-HRP conjugates, allophycocyanin, B-phycoerythrin, R-phycoerythrin, peroxidase, fluors (i.e., DyLight, Cy3, Cy5, FITC, HiLyte Fluor 555, HiLyte Fluor 647), and/or staining kits (i.e., ABC Staining Kit, Pierce)). The kits may also include other reagents and/or instructions for using the antibodies in commonly utilized assays described above such as, for example, flow cytometric analysis, ELISA, immunoblotting (i.e., western blot), in situ detection, immunocytochemistry, immunohistochemistry.

In one embodiment, the kit provides the immunoreagent (antibody or antigen) in purified form. In another embodiment, immunoreagents are provided in biotinylated form either alone or along with an avidin-conjugated detection reagent (i.e., antibody). In another embodiment, the kit includes a fluorescently labeled immunoreagent which may be used to directly detect antigen. Buffers and the like required for using any of these systems are well-known in the art and may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1

Antibody Immunity to a Panel of Oncogenic Proteins Predicts Presence of Colorectal Cancer and Stage of Disease This example describes an assay of sera from patients with colorectal cancer and healthy controls that can identify antigens which indicate presence of disease. Antigens thus identified can be incorporated into a colorectal cancer specific screening panel. The example demonstrates that a panel of antigens identified by an exploratory sample set could be validated in an independent, blinded sample set for early detection of colorectal cancer.

The following abbreviations are used herein: HER2: HER-2/neu; Cat D: cathepsin D; Top2: topoisomerase II α; CEA:

carcinoembryonic antigen; ELISA: enzyme-linked immunosorbent assay; FCS: fetal calf serum; HRP: horseradish peroxidase; OD: optical density.

A preliminary set of 30 serum samples from colorectal cancer patients with late stage disease and 100 samples from normal donors were analyzed to compare antibody responses to a panel of oncogenic proteins. Based on results, we chose a panel of 6 antigens which stimulated significantly greater antibody responses in patients than in normal donors; p53 ($p=0.002$), cathepsin D ($p=0.005$), CEA ($p=0.001$), cyclin B1 ($p<0.000$), topoisomerase II α ($p<0.001$), and IGFBP-2 ($p<0.001$). We then obtained clinically characterized, commercially collected sera from 51 patients with Stage I and Stage II colorectal cancer, and commercially collected sera from 51 age and sex matched healthy controls. Samples were coded and assayed in blinded fashion using indirect ELISA. Responses to the antigen panel were analyzed and receiver operating characteristic curves constructed to determine the ability of the panel to discriminate between patients and controls.

After unblinding, responses to p53 ($p=0.001$), cathepsin D ($p=0.006$), cyclin B1 ($p=0.003$), and IGFBP-2 ($p=0.050$) were significantly higher in early stage colorectal cancer patients than in healthy controls, and responses to topoisomerase II α ($p=0.026$) were significantly lower. Responses to CEA were not significantly different between groups ($p=0.286$). Antibody responses to p53 alone resulted in an area under the curve of 0.767. Addition of cathepsin D and then cyclin B1 to the panel resulted in areas under the curve of 0.776 and 0.801, respectively. Addition of IGFBP-2 increased the area to 0.816, and by applying a formula which subtracted topoisomerase II α specific results from the sum of the results for all other antigens, the area under the curve increased to 0.823 ($p=0.000$). At a cutoff point of 0.35, sensitivity was 90% and specificity was 46%. In addition, linear regression indicated the final panel result was a significant predictor of stage ($p=0.042$), with mean panel result for Stage II patients (2.00) more than double that for Stage I patients (0.967). These results demonstrate that responses to some oncogenic proteins can be associated specifically with early stage colon cancer, compared to late stage disease. Responses to multiple serum antibodies to colorectal cancer related antigens can serve as useful biomarkers for colorectal cancer diagnosis and disease management.

Methods

Phase I cases and controls. Samples collected after informed consent from patients with late stage colon cancer were obtained from the Tumor Vaccine Group serum repository. No clinical data was available on the patients except for age and sex. Samples from healthy donors were obtained from The Puget Sound Blood Center. Donors met all standards for blood donation, and only age and sex were known for each donor.

Phase II cases and controls. Samples from patients with early stage colorectal cancer were obtained from Asterand, Inc. Blood was collected after informed consent, and stored until time of purchase by Tumor Vaccine Group. Samples were shipped on dry ice overnight and kept frozen until time of assay. Each sample was thawed and aliquoted to vials labeled with only in in-house ID prior to assay. Samples were accompanied by clinical data on patients consisting of age, sex, stage, smoking history, history of alcohol use, current medications, height, weight, BMI, and reproductive status for women. Samples from healthy controls were obtained from ProMedDx, LLC. Blood was collected after informed consent, and stored until time of purchase by Tumor Vaccine Group. Samples were shipped on dry ice overnight and kept frozen until time of assay. Each sample was thawed and aliquoted to vials labeled with only in in-house ID prior to assay. All donors met standards for commercial blood donation, and were matched by age and sex to cases. No other data on controls were available (Table 1).

TABLE 1

Sample set characteristics

| | Phase 1 | | Phase 2 | |
|---|---|---|---|---|
| | Purpose | | | |
| | Exploratory: identify markers of interest | | Clinical validation: establish the assay detects established disease | |
| | Controls | Cases | Controls | Cases |
| Sample source | Puget Sound Blood Center | Tumor Vaccine Group repository | ProMedDx, Ltd | Asterand, Inc. |
| N | 100 | 30 | 51 | 51 |
| Disease state | Healthy donors | Late stage colorectal cancer | Healthy donors | Stage I 13 Stage II 38 |
| Sex | 52% male | 49% male | 49% male | 49% male |
| Age range | 34-76 | 18-72 | 44-89 | 44-89 |
| Total N | | 130 | | 102 |

Indirect ELISA. Measurement of serum antibodies to topoisomerase IIα, IGFBP2, cathepsin D, cyclin B, NY-ESO-1, and CEA were performed by indirect ELISA as previously described (Goodell et al., 2006, J. Clin. Oncology 24:762-768). Briefly, alternate columns on Immulon 4HBX plates were coated overnight with purified human topoisomerase IIα (Topogen, Columbus, Ohio), IGFBP2 (Sigma Chemicals Inc., St. Louis, Mo.), cathepsin D (U.S. Biological, Swampscott, Mass.), cyclin B (U.S. Biological), NY-ESO-1 (kindly provided by Dr. Brad Stone), and CEA (Protein Sciences, Meriden, Conn.), or carbonate buffer alone, blocked for 1 hour with PBS/BSA, and washed with PBS/Tween. After washing, 50 µl/well of control or experimental sera was added in duplicate titration sets. After overnight incubation at 4° C., plates were washed again and anti-human/HRP conjugate added 50 µl/well. Plates were washed again after a 45 minute incubation at 4° C. and developed using TMB reagents (KPL, Gaithersburg, Md.).

Capture ELISA. Measurement of serum antibodies to HER-2/neu and p53 were performed by capture ELISA as previously described (Goodell, J Immunol Methods 299:129-138, 2005).

A positive sample was defined as an antibody concentration above the non-parametric $95^{th}$ percentile of the control samples evaluated for each antigen. For p53 antibodies the cut-off value for positivity was 0.91 µg/ml, for HER-2/neu antibodies 1.13 µg/ml, for topoisomerase IIβ antibodies 0.32 µg/ml, for IGFBP2 0.25 µg/ml, for cathepsin D 1.25 µg/ml, for cyclin B 0.40 µg/ml, for CEA 0.85 µg/ml, and for NY-ESO-1 antibodies the positive cutpoint was 1.35 µg/ml. All indirect and capture assays were validated quality-controlled according to CLIA-mandated standards.

Statistical methods. Significance of proportional differences was quantified by Fisher's Exact Test. Two-way comparisons of antibody levels between cases and controls were analyzed by Mann-Whitney U test. Analytic performance of the multiple antigen panel assay was evaluated by plotting receiver operating characteristic (ROC) curves of results and estimating area under the curve (AUC). Linear regression of Phase I data was used to obtain a weighting value for each individual marker. For each Phase II sample, results from individual markers were weighted according to regression coefficients obtained from the Phase I data and summed. Thus, each Phase II sample (case and control) was associated with a final resulting value which could be used to create the ROC curves.

Results

Phase I

Magnitude and presence of antibodies to tumor associated antigens are greater in patients with colorectal cancer than in normal donor controls. Thirty patients with colorectal cancer and 100 normal donor controls were tested by quantitative ELISA for IgG antibodies to tumor associated antigens cyclin E, p53, cyclin B, Top2, IGFBP2, NY-ESO-1, HER2, cathepsin D and CEA (FIG. 1A). There were no differences between patients and donors for HER2 (p=0.66) and NY-ESO-1 (p=0.93), but all other antigens showed an increased response in cancer patients compared to normal donors. The greatest differences were found in responses to IGFBP-2, with a mean of 0.54 µg/ml in patients and a mean of 0.03 in donors (p<0.001); to Top2, with a mean of 0.38 µg/ml in patients and a mean of 0.10 µg/ml in donors (p<0.001); and to CEA, with a mean of 0.20 µg/ml in patients and a mean of 0.04 µg/ml in donors (p=0.001). Responses to cathepsin D were also much higher in patients than controls, with the mean for patients (1.41 µg/ml) nearly double that of the mean for donors (0.71 µg/ml) (p=0.001) Mean response to p53 was 0.2 µg/ml in patients and 0.16 µg/ml in normal donors (p=0.01), and mean response to cyclin B was 0.25 µg/ml in patients and 0.12 µg/ml in donors (p=0.004). Responses in patients ranged from 0 to 12.0 µg/ml, and in normal donors responses ranged from 0 to 3.3 µg/ml.

Figure 1B:
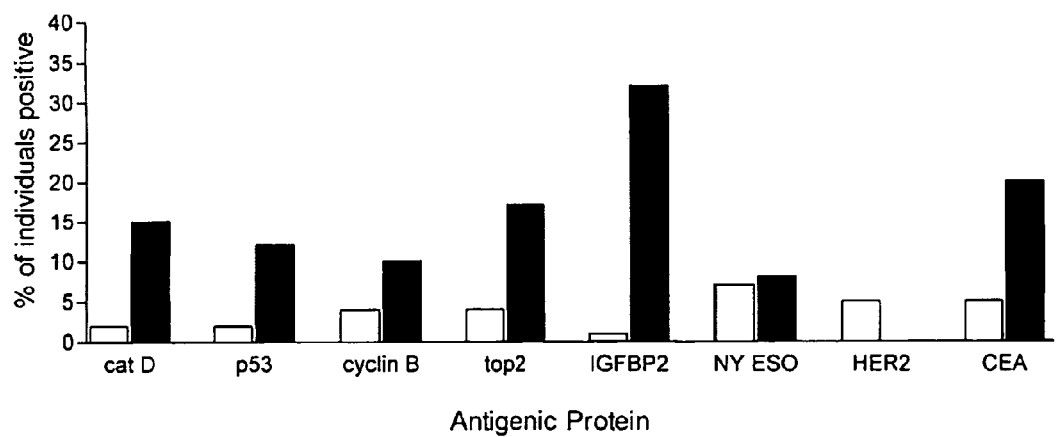
Figure 2:
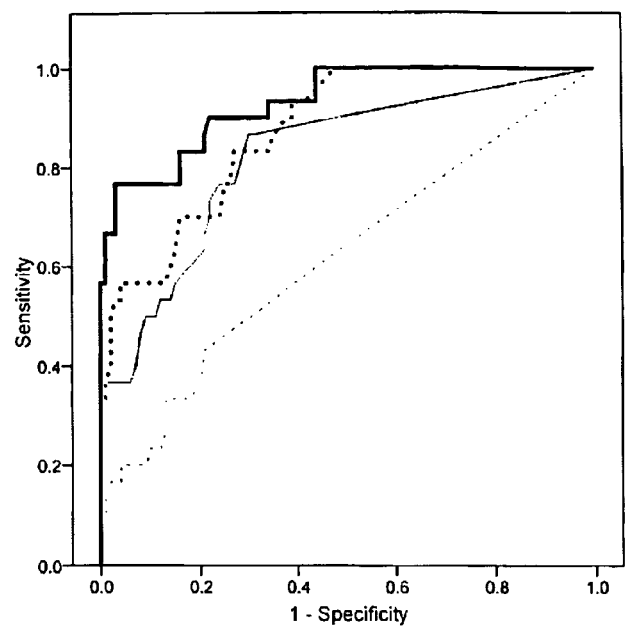
FIG. 2. Antibody responses to a panel of tumor associated antigens can distinguish between colorectal cancer patients and normal donor controls. ROC curves were plotted to examine the ability of the proposed panel of antigens to distinguish between colorectal cancer patients and normal blood donors. Shown are the sensitivity (vertical axis) versus 1-specificity (horizontal axis) for responses to p53 alone (thin broken line) p53 plus CEA (thin line), p53, CEA, Top2 and cyclin B (heavy broken line), and the final weighted sum of six antigens (heavy line).

Results were dichotomized by classing results as positive based on the 95$^{th}$ non-parametric percentile of 200 normal blood donors assayed during the validation of each assays, and the differences in percent positive tested for significance by Chi2 (FIG. 1B). We found that when ranked by this method, none of the patients were positive for antibodies to cyclin E or HER2, and that there was no difference between the proportion of NY-ESO-1 antibody-positive patients samples and the proportion of NY-ESO-1 antibody-positive donor samples (p=0.563). There was, however a wide difference in proportion of patient (31%) and donor (1%) samples positive for IGFBP2 antibodies (p<0.001), and proportion of patient (12%) and donor (2%) samples positive for p53 (p<0.001). There were also differences between the proportion of patient and donor samples positive for Top2 (17% vs. 4%) (p=0.005), CEA (20% vs. 5%) (p=0.022), and cathepsin D (20% vs. 5%) (p=0.022). In addition, we found that 50% of colorectal patients had a response to 1 antigen, 10% had responses to 2 markers, 3.3% had responses to 3 markers, and 1 patient had positive responses to 4 markers. In contrast, only 16% of normal donors had a response to one antigen, and 1.4% had responses to 2 antigens. Thus, the majority of patients (67%) had a response to at least 1 of the antigens tested, while only 17% of donors had a response to 1 antigen or more.

Antibody responses to a panel of tumor associated antigens can distinguish between colorectal cancer patients and normal donor controls. Serum samples from 30 colorectal cancer patients and 100 healthy controls were tested for responses to p53, IGFBP-2, TOPO2-α, CEA, cathepsin D and cyclin B, and responses were used to construct ROC curves. Response to CEA alone was not a significant predictor of breast cancer (AUC=0.62) (p=0.538), but combining responses to 2 antigens (CEA and IGFBP-2) resulted in an AUC of 0.82 (p=0.006), and combining responses to all antigens increased the area under the curve to 0.87 (p=0.001). We used regression analysis to find a weighting coefficient for each antigen. After applying the coefficient values to the results, we used the new combined value to plot an ROC curve with a resulting AUC of 92% (p<0.001).

Because the same set of samples was used to choose the antigens for the panel and to obtain weighting values, the ROC for Phase I sample set is subject to extreme bias, and overestimates panel diagnostic performance. In order to assess diagnostic performance in a non-biased manner, the panel assay and weighting algorithm were tested in Phase II using an independent, blinded sample set consisting of well-characterized clinical samples and matched control samples.

Phase II

Magnitude and presence of antibodies to tumor associated antigens are greater in patients with early stage colorectal cancer than in healthy controls. Fifty-one patients with colorectal cancer and 51 age and stage-matched healthy controls were tested by quantitative ELISA for IgG antibodies to tumor associated antigens p53, cyclin B, Top2, IGFBP2, cathepsin D and CEA. We found that there was no difference between case and control for responses to CEA, and no difference in responses to CEA between Stage I and Stage II colorectal cases. Responses to 4 of the antigens included in the panel stimulated greater antibody responses in cases than controls. For p53, the mean antibody response in patients was 0.06 µg/ml compared to 0.7 µg/ml in controls (p=0.001). Responses to cathepsin D were 1.0 µg/ml in cases and 0.71 µg/ml in controls (p=0.006). For cyclin B1 (p=0.003) and IGFBP-2 (p=0.050) the mean antibody response in cases was 0.28 µg/ml and 0.03 µg/ml, respectively, and in controls the means were 0.18 µg/ml and 0 µg/ml, respectively. For Top2, in comparison to results for the Phase I sample set, we found that the Phase II sample set showed a significantly decreased mean antibody response in cases compared to controls (p=0.026), with mean responses of 0.27 µg/ml in controls and 0.13 µg/ml in cases. This difference was primarily between Stage II cases and controls (p=0.050), Stage I cases and controls having identical mean responses (0.27 µg/ml). While mean responses for all antigens except CEA were higher in Stage II cases than Stage I cases, this difference was only significant for Top2.

Results from cases and controls were dichotomized according to the same method as described for the Phase I sample set. Interestingly, for 3 antigens, p53 (p=0.001), IGFBP-2 (p=0.050) and cyclin B (p=0.023) none of the control samples were classed as positive, while 22% were positive for p53 antibodies and 10% were positive for cyclin B antibodies. Only 3 of the cases were positive for IGFBP-2 antibodies (6%). For cathepsin D, 33% of cases had positive responses and 12% of controls (p=0.040). For Top2, only 6% of cases were positive (and those were all Stage I) and 16% of controls. Dichotomization of CEA specific responses resulted in a significant (p=0.023) difference in proportion positive between cases (20%) and controls (4%), due to the existence of outliers in the distribution of responses among controls. Furthermore, we found that 57% of the cases had a positive response to at least 1 antigen, 33% to 2 or more and 8% of cases responded to at least 3. Two of the cases responded to a total of 4 antigens, one Stage I and 1 Stage II. Among the controls, 24% had antibodies to at least 1 antigen, 20% to 1 antigen alone, and 2 controls responded to 2 antigens. None of the controls responded to more than 2 antigens. By stage, 53% of Stage I cases responded to 1 or more antigens, and 58% of Stage II cases responded to 1 or more antigens.

Figure 5:
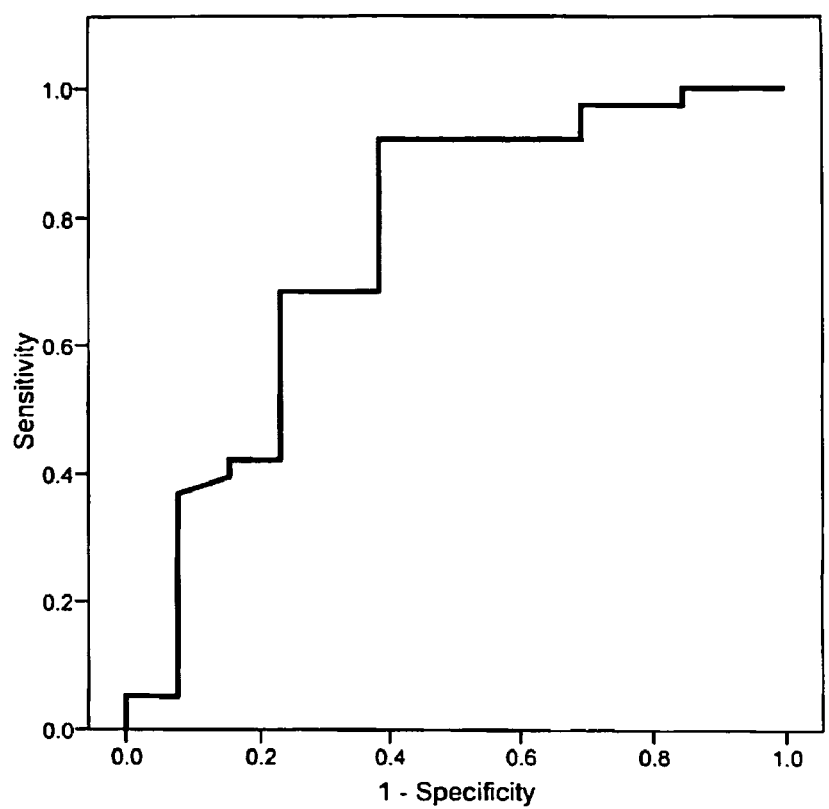
FIG. 5. Antibody responses to a panel of tumor associated antigens can distinguish between colorectal cancer patients with Stage I and Stage II disease. Panel results from 13 Stage I colorectal cancer cases and 38 Stage II colorectal cancer cases were used to construct ROC curves in order to assess the ability of the panel to distinguish between Stage I and Stage II disease. Sensitivity (vertical axis) versus 1-specificity (horizontal axis) is shown for the final weighted value (heavy line) as a predictor of Stage II vs. Stage I.

Antibody responses to a panel of tumor associated antigens can distinguish between colorectal cancer patients with early stage disease and controls without malignancy. Serum samples from 51 colorectal cancer patients with Stage I and II disease and 51 healthy controls matched for age and sex were tested for responses to p53, cyclin B, Top2, IGFBP2, cathepsin D and CEA. Responses were weighted according to the regression coefficients obtained from the Phase I data set, and used to construct ROC curves to assess diagnostic performance of the panel assay (FIG. 5). Using the summed, unweighted responses resulted in an AUC of 0.816 (p<0.001). We then applied the coefficients obtained from the Phase I data set to the Phase II results and found an area under the curve of 0.823 (95% C.I. 0.780-0.926) (p<0.001). We found that a cut point for rating a sample as positive of 0.35 achieved 90% sensitivity and 46% specificity. Sensitivity could be maximized to 94% by choosing a positive cut-point of 0.1, and specificity could be maximized to 75% by choosing a cut-point of 1.0. In this population, the optimal cut-point for positive samples resulted in 4 false negatives; that is, 4 of the colorectal cases were incorrectly classed as controls. In addition, linear regression indicated the final panel result was a significant predictor of stage (p=0.042), with mean panel result for Stage II patients (2.00) more than double that for Stage I patients (0.967).

Figure 3A:
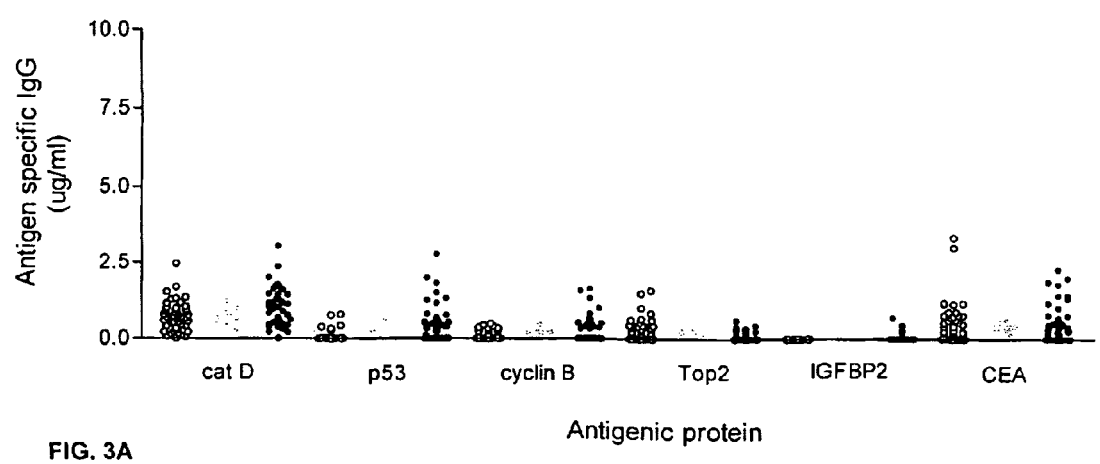
FIGS. 3A-3B. Magnitude and presence of antibodies to tumor associated antigens are higher in patients with early stage colorectal cancer than in healthy controls. (3A) Antibody responses to antigenic proteins are shown for 51 early stage colorectal cancer cases (filled circles) and 51 age and sex matched controls (clear circles). (3B) Percent of subjects with positive antibody responses to antigenic proteins are shown for 51 early stage colorectal cancer cases and 51 age and sex matched controls (clear bars).
Figure 3B:
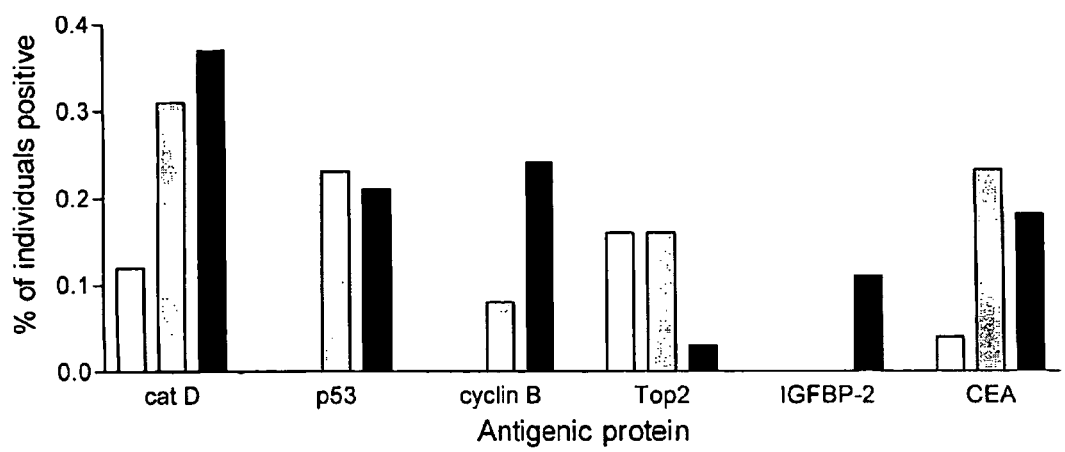
Figure 4:
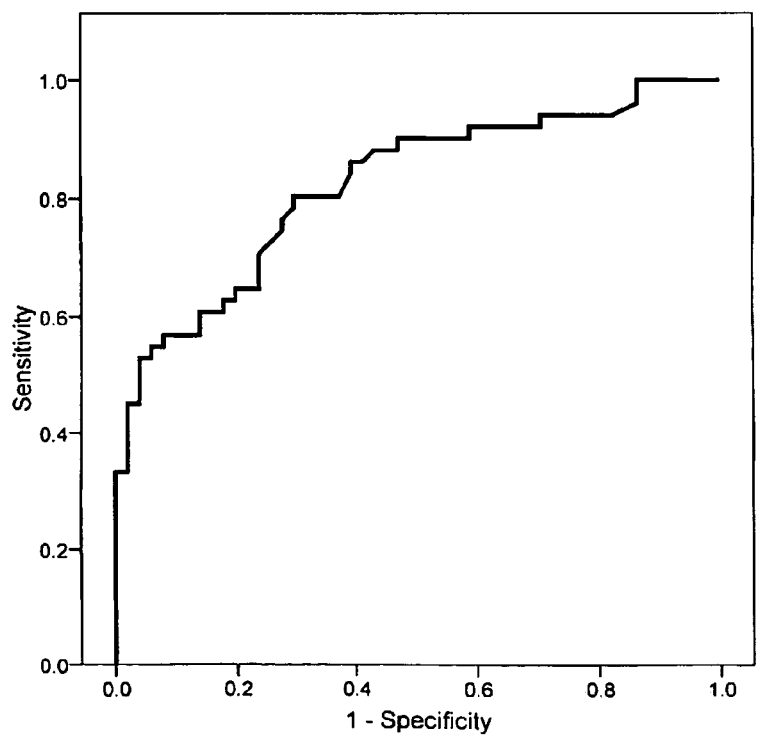
FIG. 4. Antibody responses to a panel of tumor associated antigens can distinguish between colorectal cancer patients with early stage disease and controls without malignancy. ROC curves were plotted to assess the diagnostic performance of the panel assay. Sensitivity (vertical axis) versus 1-specificity (horizontal axis) is shown for the final weighted value (heavy line) as a predictor of presence of disease.

Antibody responses to a panel of tumor associated antigens can distinguish between colorectal cancer patients with Stage I and Stage II disease. Final panel values from the 13 Stage I cases and 38 Stage II cases were used to construct ROC curves to assess the ability of the panel assay to correctly distinguish between Stage I and Stage II colorectal cancer (FIG. 3A). The ROC curve produced an AUC of 0.758 (95% C.I. 0.588-0.928) with an optimal cutpoint for classing a samples as Stage II of 0.76 (p=0.006). In this population, 84% of cases were correctly staged, with 3 of the Stage II cases incorrectly classed as Stage II and 5 of the Stage I cases incorrectly classed as Stage II.

Figure 6A:
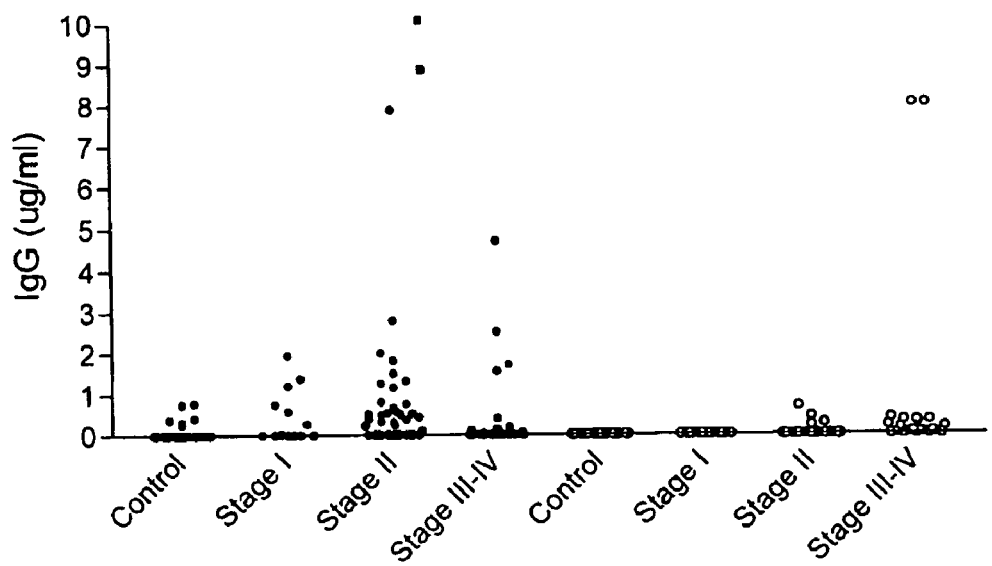
FIGS. 6A-6B. Responses to p53 and IGFBP2 alone increase as tumor burden increases, and responses to p53 and cathepsin D alone are significantly higher in Stage I compared to controls. (6A) Responses to p53 (closed circles) and IGFBP2 (open circles) increase in a stepwise fashion as stage of disease increases from healthy to Stage I, from Stage I to Stage II, and from Stage II to late stage disease. (6B) Responses to p53 and cathepsin D are higher in Stage I patients (closed circles) than in controls (open circles).

Responses to p53 and IGFBP2 alone increase as tumor burden increases, and responses to p53 and cathepsin D alone are significantly higher in Stage I compared to controls. Antibody responses to p53 increased in a stepwise fashion from 0.06 µg/ml in controls to 0.47 µg/ml and 0.72 µg/ml in Stage I and Stage II, respectively. When results from the late stage, Phase I cases were included in the analysis, the p53 specific antibody response increased again to 0.78 µg/ml, overall, a significant linear trend (p<0.001) (FIG. 6A). A similar trend was found for IGFBP2 responses when results from the Phase I cases were included (p<001), with means of 0 µg/ml found in both controls and Stage I cases. The increase in magnitude found in Stage II (0.04 µg/ml) was minimal, but in the late stage cases, the mean IGFBP2 antibody response jumped dramatically to 4.4 µg/ml.

Figure 6B:
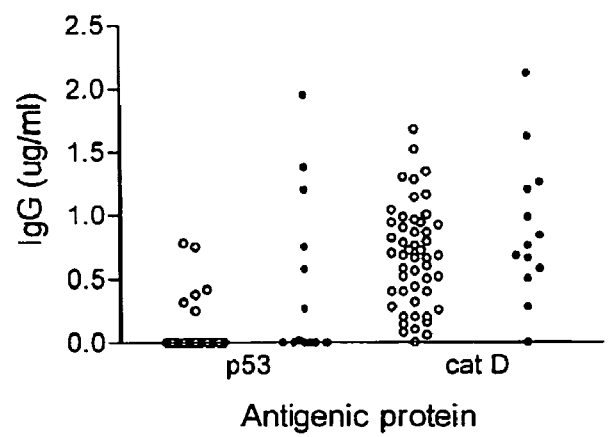
Figure 7A:
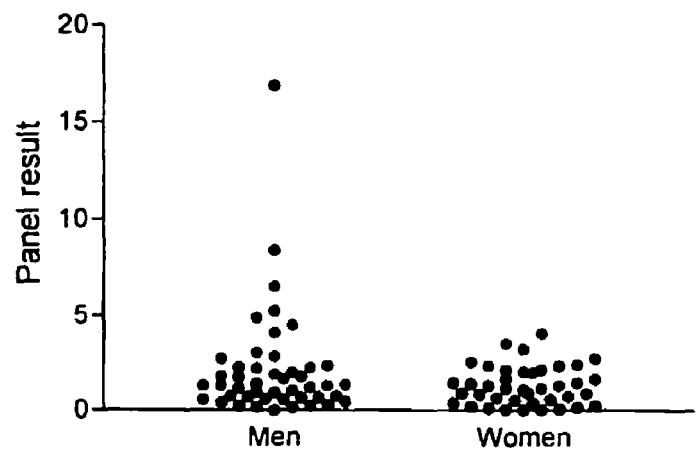
FIGS. 7A-7C. Final panel results are significantly higher in men than in women. The weighted summed total of the panel results are shown for (7A) all 50 female subjects and all 52 male subjects, (7B) the 25 female cases and 26 male cases, and (7C) 25 female controls and 26 male controls.
Figure 7B:
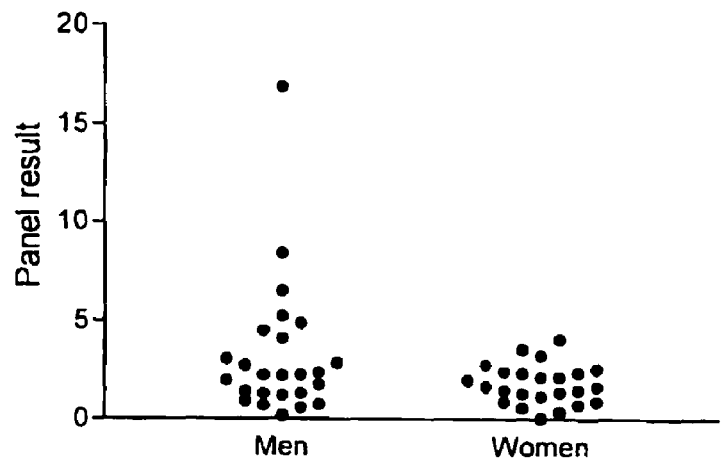
Figure 7C:

When antibody responses to controls and only those cases with Stage I disease were compared, only responses to p53 and cathepsin D were found to be significantly higher in the Stage I cases than in the controls (FIG. 6B). Responses to p53 increased from 0.06 µg/ml to 0.47 µg/ml (p=0.002) and cathepsin D responses increased from 0.71 µg/ml to 0.88 µg/ml (p=0.22). In linear regression analysis, p53 and cathepsin D results predicted presence of Stage I disease (p<0.001), with an accuracy of approximately 73% in this population.

Combined responses to antibody panel are significantly higher in men than in women. Mean panel result for male (n=52) subjects was 1.79+/−0.39, more than double the mean for female (n=50) subjects (0.88+/−0.18) (p=0.043) (FIG. 6A). When the controls were removed and only the results for the 51 cases were considered, the mean for men (n=26) was 3.07+/−0.68 and the mean for women (n=25) was 1.70+/−0.21, remaining a significant difference (p=0.050) (FIG. 6B). However, when only the matched controls were considered, the difference in means, although higher for men (0.51+/−0.18) than women (0.07+/−0.20), was not statistically significant (p=0.112) (FIG. 6C). There was a significant (p=0.018) but not powerful ($R_s$=0.331) correlation between age and IGFBP-2 specific antibody responses, but no other differences in antibody responses, as single antigens or as a panel, were found between smokers and non-smokers, alcohol users and non-alcohol users, NSAID users and non-NSAID users or between nulliparous women and parous women. There were also no other associations between immune responses and any other clinical parameters: weight, BMI, and race, smoking history, alcohol use, medication use or reproductive status (women).

Example 2

Humoral Immunity Directed against Tumor-Associated Antigens as Biomarkers for the Early Diagnosis of Cancer Many solid tumors are potentially curable if diagnosed at an early stage when the cancer can be completely surgically removed. Novel methods to aid in early diagnosis of cancer are sorely needed. A case in point is the need for early diagnosis in patients with breast cancer. Breast cancer is the most commonly diagnosed cancer in women.(1) Despite the availability of routine screening with mammography, about 40% of breast cancers, when first diagnosed, are not localized.(1) The development of new biomarkers that may help in the early detection of breast cancer will greatly facilitate the clinical management of the disease. Early detection by novel methods is critically important in younger premenopausal women whose mammograms may be compromised by increased breast density. The development of a serum-based assay that could indicate cancer exposure would be of great benefit. The detection of tumor-shed proteins in serum may be challenging due to the abundance of nonspecific serum proteins such as albumin and the requirement for larger tumor bulk to be able to detect the circulating shed protein. A promising alternative approach is to identify immune response markers, that is, serum autoantibodies that are generated in response to tumor-associated antigens (TAAs).

Tumors can express aberrant levels of mutated or modified forms of proteins that are associated with malignant growth. Such proteins can be immunogenic and stimulate cellular and humoral immune responses.(2-4) A number of TAAs, which elicit humoral immunity, have been identified in cancer patients, particularly breast cancer.(2, 5, 6) Autoantibody responses to TAAs are currently being investigated as potential diagnostic tools in multiple cancer types and are associated with several characteristics which would facilitate assay development. Serum antibody is stable, and can be readily detected with well-validated secondary antibodies.(7) Furthermore, B cells can produce specific antibodies in large amounts after stimulation by a small amount of tumor antigen.(8) As a result, TAA-specific serum antibodies can be detected at high titer in patients with early stages of cancer.(2)

The following abbreviations are used in this example: CLIA, Clinical Laboratory Improvement Act; DCIS, ductal carcinoma in situ; HER-2/ne, protein product of the erb-b2 gene, human epidermal growth factor receptor 2: MUC1, mucin 1; PAGE, polyacrylamide gel electrophoresis; ROC, receiver operating characteristic; SEREX, serological analysis of recombinant cDNA expression libraries; TAA, tumor associated antigen.

Methods to Identify Serum Autoantibodies as Potential Diagnostic Biomarkers

The successful identification of serum antibody markers is dependent on the development of high-throughput screening assays. The recent advances in proteomic technologies such as mass spectrometry and protein array have greatly facilitated the discovery of new antibody markers in cancer patient serum.(9) Both DNA- and protein-based techniques have been useful in identifying autoantibody biomarkers.

A powerful technique that has resulted in the identification of over 2000 immunogenic TAAs is Serological Screening of cDNA Expression Library (SEREX). SEREX was first developed by Sahin et al.(10) about 10 years ago. In this approach, a cDNA library is constructed using RNA from tumor specimens packaged into λ-phage vectors and expressed recombinantly in Escherichia coli. Recombinant proteins are transferred onto nitrocellulose membranes. The membranes are incubated with sera from cancer patients or control donors. The clones that are only reactive to serum from cancer patients are subcloned to monoclonality, and the nucleotide sequence of the inserted cDNA is determined.(11, 12) Multiple breast cancer antigens have been identified using SEREX, including NY-BR-1 through NY-BR-7,(3, 13) cancer-testis antigens NY-ESO-1 and SSX2,(14) ING1-a candidate breast cancer suppressor gene,(14) fibulin,(15) hMena, (16) lactate dehydrogenase-A (LDH-A),(15) thyroid hormone-binding protein (THBP),(15) and replication-protein A,(17) to name a few. The diagnostic value of these SEREX-identified antigens remains to be tested in large-scale studies. Furthermore, it is unknown how the use of E. coli as the protein expression system affects the identified antigenic repertoire. Most likely a significant number of antigens cannot be adequately identified using this technique.

Two-dimensional polyacrylamide gel electrophoresis (2D PAGE) can be used to separate thousands of individual cellular proteins from tumor tissue or cell lines. The separated proteins are transferred onto membranes. The membranes are probed with sera from cancer patients or normal donors. The proteins that only react with sera from cancer patients will be identified by mass spectrometric analysis and/or amino acid sequencing. With this method, antibodies to RS/DJ-1, an oncogenic protein that regulates RNA-protein interaction, were identified in the sera from breast cancer patients.(18) A limitation of this strategy is its relatively low throughput.(19)

A high-throughput approach to autoantibody discovery is protein array as robotic microarray spotters allow the grouping of thousands of proteins, in replicate, onto a single glass slide and make it possible to evaluate the presence of serum antibody to hundreds of proteins simultaneously. Several protein microarray platforms have been developed for high-throughput analysis. The recombinant protein arrays use clones from cDNA expression libraries or peptide phage display libraries;(20-22) the native protein arrays use proteins derived from tumor tissue or cell lines.(23, 24) Recent studies on prostate,(20) lung,(21) ovarian,(25) and breast cancer(26) have used the phage display technology. This approach involves the construction of a T7 cDNA phage display library from tumor tissue or a cell line. The candidate antigen peptides are expressed and displayed on the surface of a phage. The advantage of this approach is that the libraries can be enriched with peptides specifically recognized by patient serum using a process called biopanning before they are spotted on the array. Biopanning entails successive rounds of immunoprecipitation of phage libraries using patient serum to select the peptides recognized by antibodies in patient serum and using normal donor serum to remove the peptides recognized by antibodies in normal serum.(20, 27, 28) The limitation is that the peptide sequence is short and the immunogenicity of the noncoding sequence as detected in some the studies may be difficult to interpret.(20) Using bacteria or virus-expressed full-length recombinant proteins allows the study the immunogenicity of candidate antigens at a whole protein level, but still misses post-translational modifications such as phosphorylations and glycosylations, which may be essential to the immunogenicity of the proteins. In that respect, arraying proteins isolated from tumors or tumor cell lines may be better suited for uncovering immunogenic proteins. Fractionated proteins from a tumor cell lysate can be used to spot the array.(23, 24) In the study by Qiu et al., protein lysates from the A549 human lung adenocarcinoma cell line were separated into 1840 fractions that were spotted in duplicate, along with various controls, on nitrocellulose-coated slides. Sera from lung cancer patients and healthy controls were each hybridized to an individual microarray. The intensity measures of duplicate spots (within-slide) and duplicate slides (between-slides) were highly reproducible, exhibiting correlation values >0.9.(23) The disadvantage of this method is that each spot on the array may have multiple proteins, and subsequent identification of the individual immunogenic protein can be challenging. The inability to control protein orientation during immobilization also remains a limitation.(29) Similar to SEREX, the candidate markers that emerged from protein array screening remain to be validated in large populations.

High-throughput technologies have now allowed the identification of hundreds of candidate autoantibodies for use as biomarkers. While array-based approaches are being developed as diagnostic assays, we hypothesize that only a limited number of autoantibodies may be needed for adequate sensitivity and specificity. The identification of a limited panel of antigens that may provide broad population coverage within a specific malignancy will allow the development of clinical grade ELISA assays, greatly facilitating clinical application. The ability to develop a successful diagnostic assay, however, is dependent on several factors such as the ability to detect the autoantibody in the premalignant state, the prevalence of the autoantibody in a specific population, or even the specificity of the autoantibody for a specific tissue type. Population-based studies of individual autoantibodies can give some indication of whether the detection of humoral immunity may aid in discriminating cancer patients from noncancer bearing individuals.

Autoantibodies in Breast Cancer

Table 2 shows the frequency of autoantibodies associated with known breast cancer antigens. Serum antibodies to a few of most well-studied breast cancer antigens, p53, HER-2/neu, and MUC1, will be discussed below, and from these descriptions, some general conclusions can be drawn as to characteristics which may prioritize a candidate autoantibody for diagnostic development.

TABLE 2

Serum Antibody Responses to TAAs Detected in Breast Cancer Patients

| Tumor antigen | Serum antibody positivity in breast cancer patients | References |
|---|---|---|
| HER2 | 11% | Disis et al.(2) |
|  | 55% | Disis et al.(51) |
|  | 7% | Disis et al.(52) |
| P53 | 48% | Willsher et al.(6) |
|  | 46% | Regele et al.(53) |
|  | 26% | Green et al.(54) |

TABLE 2-continued

Serum Antibody Responses to TAAs Detected in Breast Cancer Patients

| Tumor antigen | Serum antibody positivity in breast cancer patients | References |
|---|---|---|
| | 26% | Mudenda et al.(55) |
| | 21% | Gao et al.(56) |
| | 5% | Angelopoulou et al.(57) |
| | 15% | Regidor et al.(58) |
| | 12% | Peyrat et al.(59) |
| | 8% | Dalifard et al.(60) |
| | 9% | Crawford et al.(5) |
| | 10% | Goodell, unpublished |
| MUC1 | 8% | Kotera et al.(61) |
| | 26% | von Mensdorff-Pouilly et al.(46) |
| | 20-23% | Chapman et al.(50) |
| | 20% | Goodell, unpublished |
| Endostatin | 42-66% | Bachelot et al.(62) |
| Lipophilin B | 27% | Carter et al.(63) |
| HSP90 | 37% | Conroy et al.(64) |
| Cyclin B1 | 43% | Suzuki et al.(65) |
| Fibulin | 75% | Pupa et al.(66) |
| Cyclin D1 | 8% | Goodell, unpublished |
| Cathepsin D | 5% | Goodell, unpublished |
| TOPO2α | 7% | Goodell, unpublished | p53 is one of the most extensively studied tumor antigens. It is an approximately 53 kDa nuclear phosphoprotein which normally plays the role of tumor suppressor as an intermediary of natural cell death. Wild-type p53 acts in a dominant fashion to suppress uncontrolled cell growth, serving as a mediator of cell cycle arrest or apoptosis. In normal cells, p53 is present at a very low level and exclusively in the nuclei. p53 mutations can occur in up to 50% of all cancers.(30) Mutation inactivates normal function, resulting in 'immortalized' cells. Mutant p53 accumulates in the cancer cell cytosol and nucleus and, thus, is specific to cancer cells. Many studies have shown that p53 mutations may occur early in the transformation of some cancers, an essential characteristic for use as an early cancer detection tool.(26, 27) Increased p53 protein in tumor cells is indicative of a mutated p53 gene, and the increased level of p53 may elicit an immune response resulting in anti-p53 autoantibody in serum.(31, 32) Antibodies against the p53 protein have been detected in the serum of patients with many cancers such as breast cancer, Burkitt's lymphoma, lung cancer, and pancreatic cancer.(33) There is a strong correlation between accumulation of p53 in primary tumor cells and presence of serum p53-specific antibodies in patients with different tumor types.(34)

Multiple studies have focused on the evaluation of autoantibodies to p53 as a diagnostic tool due to reports suggesting that the antibody responses to p53 can occur early in the course of a cancer and predict undetected malignancy or premalignancy. One of the earliest reports described the evolution of the p53 antibody response in patients at high risk of developing lung cancer, heavy smokers.(35) Although study subjects were free of cancer at the time antibody assessment started, rising titers of p53 antibodies preceded the development of early stage lung cancers bearing p53 mutations in two patients. Additional studies have shown that p53 specific antibodies can be detected prior to clinical diagnosis of cancer. (36, 37) Serum p53 antibodies have been detected in 11.6% (5/43) of early stage breast cancer patients with ductal carcinoma in situ of the breast, a preinvasive lesion. Three of the 5 seropositive patients had lesions no larger than 5 mm.(38)

The detection of autoantibodies may be used as an adjunct to more standard serologic tests being evaluated to aid in cancer diagnosis. Muller et al. showed that the addition of p53 specific antibody detection to conventional tumor markers (CEA for colon cancer, AFP for hepatocellular carcinoma, CEA and CA15-3 for breast cancer, CA72-4 for gastric cancer) led to an increase in diagnostic sensitivity of 8% without decreasing specificity.(39) The methods to measure anti-p53 antibody in serum are straightforward. The recombinant protein is available through a commercial source. Furthermore, a cell lysate-based assay that utilizes BT-20, a cell line that overexpresses p53, to measure anti-p53 has also been developed to be Clinical Laboratory Improvement Act (CLIA)-compliant.(40) The disadvantage of the use of p53 humoral immunity as a single biomarker is the lack of specificity for any particular cancer.

Another well-known TAA for breast cancer is HER-2/neu. HER-2/neu is an approximately 185 kDa protein and is a member of the epidermal growth factor receptor group, a transmembrane phosphoglycoprotein receptor presumed to act as a growth factor receptor. The nonmutated protein is expressed at low levels in normal cells but constitutively overexpressed at high levels by malignant cells. The gene for HER-2/neu is present in many normal tissues as a single copy. Amplification of the gene (rather than mutation) and/or overexpression of the protein on the cell surface has been identified in multiple cancers. Protein overexpression occurs in approximately 30% of breast cancers, particularly premenopausal breast cancer, and is associated with more aggressive disease and a poor prognosis in patients with positive lymph nodes.(41)

Similar to investigations of antibody response to p53, endogenous humoral immunity to HER-2/neu directly correlates to overexpression of the protein by the patient's tumor, and HER-2/neu-specific autoantibodies can be detected in patients with early stage disease, indicating that the presence of antibodies are not simply a reflection of tumor burden. HER-2/neu antibodies at titers of >1:100 were detected in 12 of 107 (11%) breast cancer patients versus 0 of 200 (0%) controls (p<0.01).(2) Detection of antibodies to HER-2/neu also correlated to overexpression of HER-2/neu protein in the patient's primary tumor. Nine of 44 (20%) patients with HER-2/neu positive tumors had HER-2/neu-specific antibodies, whereas 3 of 63 (5%) patients with HER-2/neu-negative tumors had detectable antibodies (p=0.03). Furthermore, we have recently shown that antibodies are associated with the extent of protein overexpression in primary tumor.(42) The presence of HER-2/neu-specific antibodies in breast cancer patients and the correlation with HER-2/neu-positive tumors implies that immunity to HER-2/neu develops as a result of exposure of patients to HER-2/neu protein expressed by their own cancer.

HER-2/neu specific autoantibodies have been found in the sera of patients with colon cancer, and, again, their presence correlates with overexpression of protein in the primary tumor (p<0.01).(43) HER-2/neu has also been demonstrated to be a shared tumor antigen in patients with prostate cancer. Antibody immunity to HER-2/neu was significantly higher in patients with prostate cancer (15.5%, 31/200) compared with controls (2%, 2/100, p=0.0004), and titers greater than 1:100 were most prevalent in the subgroup of patients with androgen-independent disease (16%, 9/56).(44) Studies such as those described here provide the basis for evaluating antibodies to HER-2/neu as a potential tool for cancer diagnostics, but also underscore the questionable utility of single antibody evaluation for diagnosis. Although the specificity of the approach may be significant, that is, few responses are found in noncancer bearing individuals, the sensitivity of antibodies to identify all patients with HER-2/neu overexpressing tumors is low.

Similar to HER2, MUC1 is also expressed on the cell surface. Mucins are a family of glycoproteins with high molecular weight that have a large number of tandem repeat domains that vary in length. MUC-1 has been found to be expressed abundantly in many epithelial tumors including the majority of breast cancers,(45) and circulating immune complex containing polymorphic epithelial mucin has been detected in breast cancer patients and patients with benign breast tumors.(46, 47) An evaluation of the immunogenicity of MUC1, however, identifies a significant potential obstacle in the use of autoantibodies for cancer diagnosis. A large study, involving 101 patients with breast cancer, 40 women with benign breast tumors and 96 healthy controls, suggested that MUC1-specific antibody immunity was found more often among women with benign disease than in women with breast cancer. Indeed, a negative correlation was found between presence of MUC1 antibodies and extent of disease, such that the rate of positive response dropped from 38% in women with nonmalignant lesions to 26% in women with newly diagnosed breast cancer. A further drop to 18% was found in women with recurrent or progressive breast cancer. Earlier this year, the same investigators went on to demonstrate that within a population of 127 women with BRCA1 or BRCA2 mutations, MUC1 antibody levels were significantly lower than those found in 370 age-matched controls.(48)

These clinical reports of autoantibodies against TAA detected in cancer patients with much higher frequency than control donors demonstrate that autoantibodies can be raised against both intra- and extracellular proteins, that circulating autoantibodies can be found in both early stage as well as preinvasive tumors, and that TAA autoantibodies can be identified in high risk patients who are not yet tumor bearing. All these characteristics would be a benefit for a diagnostic assay. However, autoantibodies can also be associated with benign disease or even be detected at lower levels in tumor bearing individuals than controls. Moreover, measurement of a single autoantibody will not provide the adequate sensitivity needed for a diagnostic test. These observations underscore the need to fully characterize an autoantibody response across multiple populations prior to clinical development.

Detecting Serum Antibody Response to a Panel of TAAs

Figure 8:
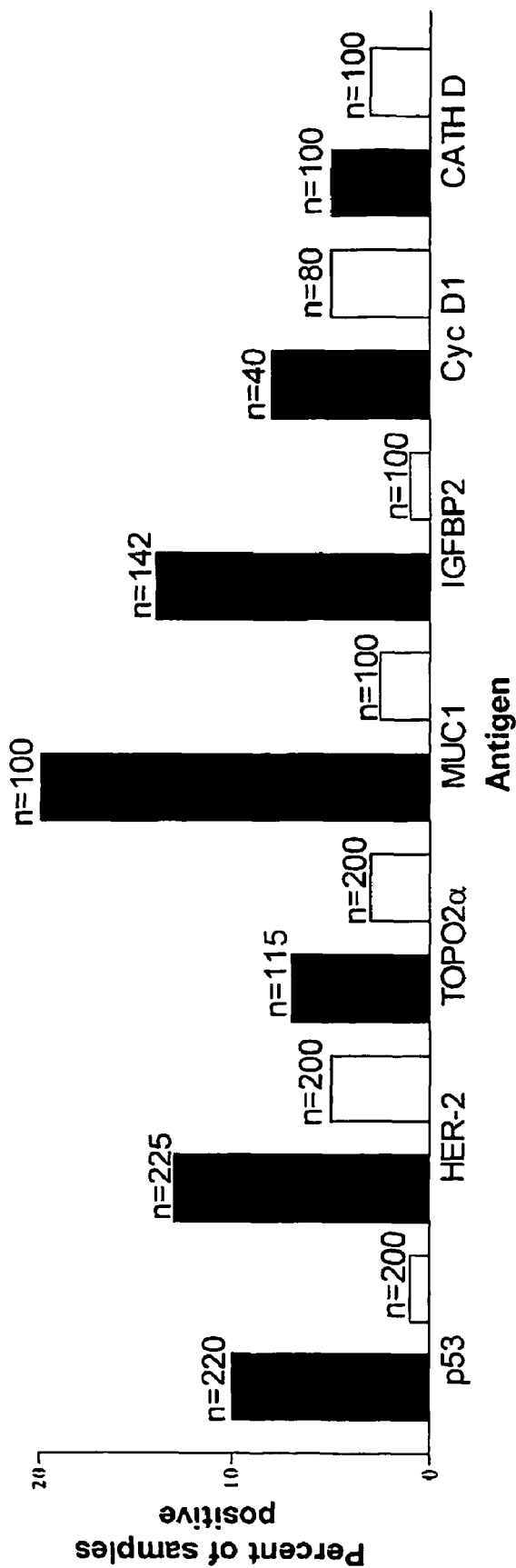
FIG. 8. Antibodies to tumor associated antigens are more frequently detected in sera from breast cancer patients than from normal donors. Shown are the percentages of individuals positive for serum antibody to 7 tumor antigens. Gray columns show the response in patients; white columns show the response in control normal donors. The number of patients or controls tested for each antigen were indicated at the top of the column. The antibody responses to TOPO2α, IGFBP2, cathepsin D (CATH D), MUC1, and cyclin D1 were measured using recombinant ELISA. The antibody responses to p53 and HER2 were measured using capture ELISA. A sample was defined as positive if the antibody concentration was greater than the mean ±3SD of the reference population.

The use of a single antibody as predictor of disease exposure has obvious limitations because the test is only valid to patients whose tumors harbor the antigens. For example, anti-p53 antibodies have been studied in over 9489 patients with a wide variety of tumors.(36) Despite the strong specificity of the response, only 20-40% of patients with cancers harboring p53 missense mutations will have p53 antibodies in their sera. Since no single serum antibody marker exists in all the patients, we seek to identify a combination of markers that may increase patient coverage. This statement is based on the assumption that multiple serum antibodies specific to these TAAs can be detected simultaneously from the same patient. Our laboratory has developed multiple CLIA-compliant ELISA assays to measure TAA-specific antibodies in serum. (40. 49) We recently investigated the serum antibody response to 7 well-characterized TAAs (p53, HER2, MUC1, topoisomerase II alpha (TOPO2α), insulin-like growth factor binding protein 2 (IGFBP2), Cyclin D1, and cathepsin D) in a heterogeneic breast cancer population and control age- and gender-matched donors using validated ELISA assays (FIG. 8). Approximately 18% of the breast cancer patients had early stage disease and approximately 82% had late stage disease. Patients were between the ages of 18-75. The controls met all requirements for donation to the regional blood center and were between the ages of 18 and 75. The antibodies to TOPO2α, IGFBP2, and cathepsin D were measured by indirect ELISA using commercially available recombinant proteins as previously described.(49) Briefly, alternate columns on 96-well plates were coated overnight with purified human TOPO2α (Topogen, Columbus, Ohio), IGFBP2 (Sigma Chemicals, Inc., St. Louis, Mo.), cathepsin D (U.S. Biological, Swampscott, Mass.), MUC1 (Abnova, Corp., Taipei), cyclin D1 (Research Diagnostics, Inc., Concord, Mass.), or carbonate buffer alone, blocked for 1 h with PBS/BSA, and washed with PBS/Tween. After washing, 50 μL/well of control or experimental sera was added in duplicate titration sets. After overnight incubation at 4° C., plates were washed again and anti-human/HRP conjugate was added at 50 μL/well. Plates were washed again after a 45 min incubation at 4° C. and developed using TMB reagents (KPL, Gaithersburg, Md.). The antibody responses to HER-2/neu and p53 were performed by capture ELISA as previously described.(40) Briefly, 96-well plates were coated with 520-C9 (monoclonal antibody to HER2) or TIB-116 (monoclonal antibody to p53) before the addition of SKBR3 cell lysate (HER2+) or BT-20 cell lysate (p53+) which serve as antigen sources. Serially diluted, purified human IgG provided a standard curve. A sample was defined as positive if the value was greater than mean ±2SD (for HER2) or mean ±3SD (for p53) of the previously analyzed reference population which were shown to be negative by Western blot analysis. Positive results for each assay were confirmed by Western blot analysis. With the use of Western blot as gold standard, the sensitivity of the assays is 77% (HER2) and 100% (p53), and the specificity of the assay is 89% (HER2) and 93% (p53).

As shown in FIG. 8, we have found that breast cancer patients have increased antibody response to p53, HER2, MUC1, topoisomerase II alpha (TOPO2α), insulin-like growth factor binding protein 2 (IGFBP2), Cyclin D1, and Cathepsin D. The most frequently found antibody response was directed against MUC1, which was detected in 20% of the patients, compared to a responses rate in controls of approximately 3%. Thirteen percent and 10% of breast cancer patients had antibodies to HER-2/neu and p53, respectively, while only 5% of controls had antibodies to HER-2/neu and only 1% of controls had p53-specific antibody responses. Cyclin D1 antibodies were found in 8% of patients, TOPO2α antibodies were found in 7% of patients, and 5% of patients had cathepsin D autoantibodies. Cathepsin D antibodies and TOPO2α antibodies were found in 3% of controls, and 5% of controls had cyclin D1 antibodies. Antibodies specific for tumor-associated antigens were found in patients with both early and late stage disease. This data demonstrates that breast cancer patients can generate immune responses to multiple antigens simultaneously. Although the serum antibody response rate to the best performing single antigen, MUC1, is no more than 20%, addition of HER-2/neu to the panel increased the percent of positive samples to 25%, and addition of p53 and IGFBP2 increased the rate of positivity to 31%. Thus, 31% of the breast cancer patients analyzed have serum antibodies to at least 1 of 4 antigens tested, suggesting that diagnostic sensitivity may be improved by using a panel of serum antibodies for detection of malignancy.

Recent publications support the idea of using a combination of autoantibody markers for cancer diagnosis. Using a phage display library constructed from prostate cancer tissue, Wang et al. analyzed serum samples from 119 prostate cancer patients and 138 control using protein array. Serum antibody responses to the 22 phage-displayed peptide detector, as built from the training set of samples, could discriminate subjects with prostate cancer and a control group with 88% specificity and 82% sensitivity.(20) Moreover, assessment of serum antibody immunity performed better in distinguishing prostate cancer from controls than assessment of serum prostate-specific antigen levels, the currently used screening test for prostate cancer.(20) However, only 4 out of the 22 peptides were derived from in-frame, named coding sequences. The remaining phage peptides were generated from untranslated sequences. A caveat to the phage display and protein array data is that the peptide antigens identified from each study may be dependent on the tumor specimen used for the construction of library and the serum used for biopanning. The biologic meaning of the noncoding sequences identified in some of the studies is also difficult to interpret.

Figure 9:
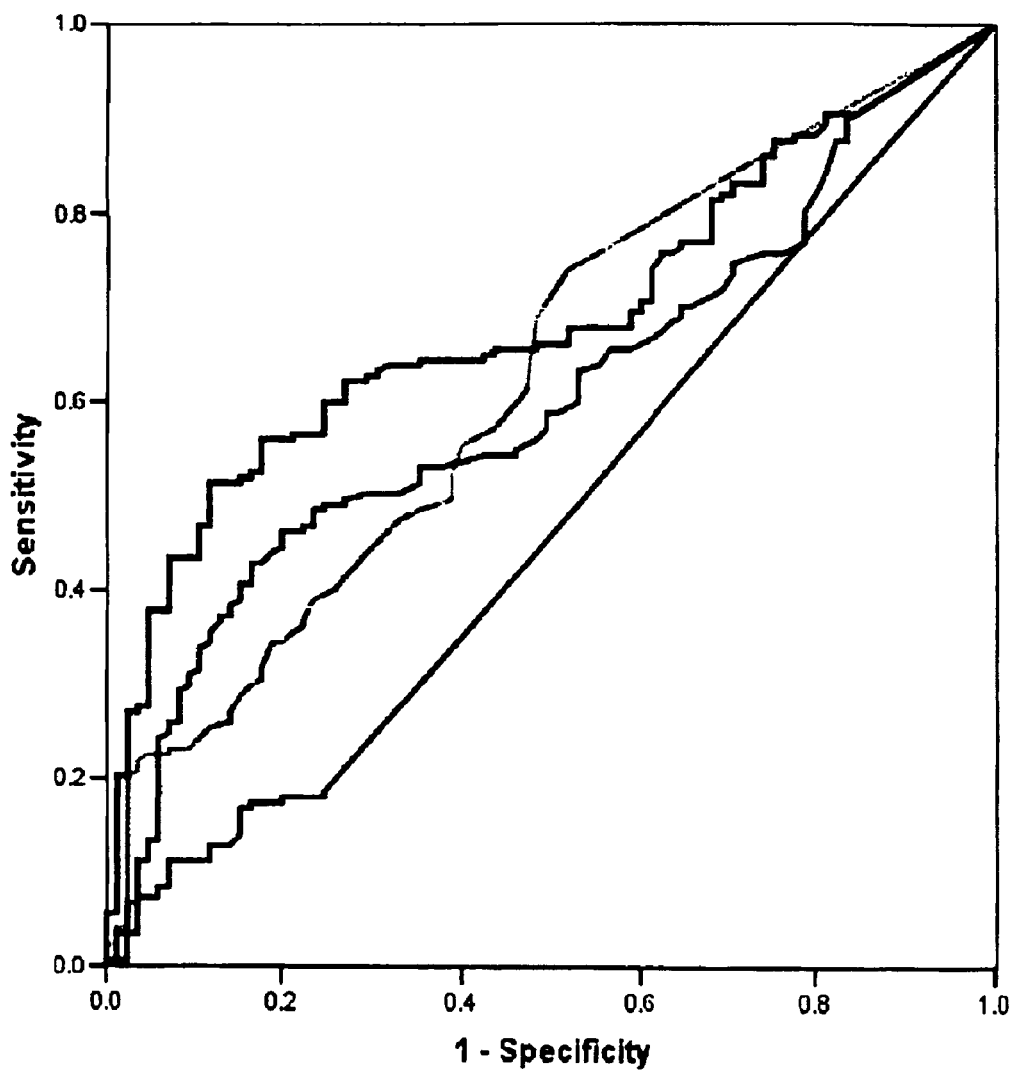
FIG. 9. Antibody responses to a panel of tumor-associated antigens can distinguish between breast cancer patients and healthy controls. Serum samples from 184 breast cancer patients and 134 healthy controls were tested for responses to p53, HER2, IGFBP-2, and TOPO2α, and responses were used to construct ROC curves. Response to p53 alone was not a significant predictor of breast cancer (AUC=0.48, p=0.538, blue line), but combining responses to 2 antigens (p53 and HER-2) resulted in an AUC of 0.61 (p=0.006, green), and combining responses to all 4 antigens increased the area under the curve to 0.63 (p=0.001, red). Using an algorithm weighted on logistic regression coefficients of independent antibody markers resulted in an AUC of 70% (p<0.001, purple).

We questioned whether a combination of well-defined antibody markers for breast cancer may have improved sensitivity and specificity over using a single marker to discriminate cancer versus controls. As shown in FIG. 9, samples from 184 breast cancer patients with late stage disease and 134 controls without malignancy were tested for responses to p53, HER-2/neu, IGFBP-2, and TOPO2α, and responses were used to construct receiver operating characteristic (ROC) curves. Data presented here indicates that response to p53 alone was not a significant predictor of breast cancer (AUC=0.48, p=0.538), but combining responses to 2 antigens (p53 and HER-2/neu) resulted in an AUC of 0.61 (p=0.006), and combining responses to all of the 4 antigens increased the area under the curve to 0.63 (p=0.001). Using an algorithm weighted on logistic regression coefficients of independent antibody markers resulted in an AUC of 70% (p<0.001, FIG. 9). This data suggests that a panel of autoantibodies is more efficient at discriminating cancer from controls than the use of a single antibody measurement. It has to be emphasized that most of the serum samples were obtained from patients with late stage disease. Whether the findings apply to early stage patients remains to be investigated. It is also noted that most of the patients in our study have received previous treatment for their disease. It is important to validate the markers in the future using samples from newly diagnosed breast cancer patients. A recent publication by Chapman et al. also tested 137 patients for antibodies to a panel of 6 antigens (p53, MUC1, c-myc, NY-ESO-1, BRCA2, and HER-2/neu) and found that a total of 64% and 45% of patients with primary breast cancer and DCIS, respectively, were positive for at least 1 of the 6 antigens. Response rates to single antigens in this population ranged from 3% to 34%, but response rates for healthy controls were not reported.(50) Although preliminary, these data support further investigation to develop a multiplexed serum antibody based assays for breast cancer diagnosis.

It is well-recognized that the immune surveillance against cancer can lead to the generation of serum antibodies recognizing TAAs, even at early stage of the disease. As summarized in this review, multiple TAA-specific serum antibodies have been reported in breast cancer patients. Preliminary data presented here as well as published data on other types of cancer support the idea of developing a serum assay evaluating the antibody response to a panel of tumor antigens for breast cancer diagnosis. The ideal screening assay will be easy to perform and compliant with CLIA standards. With the availability of novel high-throughput technologies such as phage display and protein array, multiple candidate markers have emerged. These candidates will need to be validated in larger populations with a comparison to known autoantibody markers to determine which biomarkers have the highest diagnostic value. Furthermore, candidate biomarkers must be characterized as to whether the autoantibody is detected in early invasive or even preinvasive disease. The availability of well-characterized serum samples from newly diagnosed patients and samples collected before the clinical onset of disease will be fundamental to the validation of some of the candidate markers as described in the paper. Despite the challenges that lie ahead, the assessment of a panel of autoantibodies specific for TAA holds great potential as a new diagnostic tool in the fight against cancer.

References
1. American Cancer Society, Cancer Facts and Figures 2006; American Cancer Society: Atlanta, Ga., 2006.
2. Disis, M. L.; et al., J. Clin. Oncol. 1997 15 3363 3367
3. Jager, D.; et al., Cancer Immun. 2002 2 5
4. Scanlan, M. J.; et al., Cancer Immun. 2001 1 4
5. Crawford, L. V.; et al., Int. J. Cancer 1982 30 403 408
6. Willsher, P. C.; et al., Anticancer Res. 1996 16 927 930
7. Anderson, K. S.; et al., J. Proteome Res. 2005 4 1123 1133
8. Hanash, S., Nat. Biotechnol. 2003 21 37 38
9. Shin, B. K.; et al., J. Mammary Gland Biol. Neoplasia 2002 7 407 413
10. Sahin, U.; et al., Proc. Natl. Acad. Sci. U.S.A. 1995 92 11810 11813
11. Sahin, U.; et al., Curr. Opin. Immunol. 1997 9 709 716
12. Tureci, O.; et al., Methods Mol. Med. 2005 109 137 154
13. Jager, D.; et al., Cancer Res. 2001 61 2055 2061
14. Jager, D.; et al., Cancer Res. 1999 59 6197 6204
15. Forti, S.; et al., Breast Cancer Res. Treat. 2002 73 245 256
16. Di Modugno, F.; et al., Int. J. Cancer 2004 109 909 918
17. Tomkiel, J. E.; et al., Clin. Cancer Res. 2002 8 752 758
18. Le Naour, F.; et al., Clin. Cancer Res. 2001 7 3328 3335
19. Hanash, S., Proteomics 2003 3 2075
20. Wang, X.; et al., N. Engl. J. Med. 2005 353 1224 1235
21. Zhong, L.; et al., Am. J. Respir. Crit. Care Med. 2005 172 1308 1314
22. Sreekumar, A.; et al., J. Natl. Cancer Inst. 2004 96 834 843
23. Qiu, J.; et al., J. Proteome Res. 2004 3 261 267
24. Bouwman, K.; et al., Proteomics 2003 3 2200 2207
25. Chatterjee, M.; et al., Cancer Res. 2006 66 1181 1190
26. Sioud, M.; Hansen, M. H., Eur. J. Immunol. 2001 31 716 725
27. Fossa, A.; et al., Cancer Immunol. Immunother. 2004 53 431 438
28. Minenkova, O.; et al., Int. J. Cancer 2003 106 534 544
29. Hanash, S. M.; et al., Leukemia 2002 16 478 485
30. Bueter, M.; et al., Int. J. Oncol. 2006 28 519 525
31. Davidoff, A. M.; et al., Proc. Natl. Acad. Sci. U.S.A. 1991 88 5006 5010
32. Winter, S. F.; et al., Cancer Res. 1992 52 4168 4174
33. Cho-Chung, Y. S., Biochim. Biophys. Acta 2006 1762 587 591
34. Lechpammer, M.; et al., Int. J. Colorectal Dis. 2004 19 114 120
35. Lubin, R.; et al., Nat. Med. 1995 1 701 702
36. Li, Y.; et al., Int. J. Cancer 2005 114 157 160
37. Trivers, G. E.; et al., Clin. Cancer Res. 1996 2 1767 1775
38. Regele, S.; et al., Br. J. Cancer 1999 81 702 704
39. Muller, M.; et al., Int. J. Oncol. 2006 29 973 980
40. Goodell, V.; Disis, M. L., J. Immunol. Methods 2005 299 129 138
41. Menard, S.; et al., J. Cell. Physiol. 2000 182 150 162
42. Goodell, V.; et al., Mol Cancer Ther, 2008, in press.
43. Ward, R. L.; et al., Hum. Immunol. 1999 60 510 515
44. McNeel, D. G.; et al., J. Urol. 2000 164 1825 1829
45. Rakha, E. A.; et al., Mod. Pathol. 2005 18 1295 1304
46. von Mensdorff-Pouilly, S.; et al., Eur. J. Cancer 1996 32A 1325 1331

47. Gourevitch, M. M.; et al., Br. J. Cancer 1995 72 934 938
48. Hermsen, B. B.; et al., Eur. J. Cancer 2007 43 1556 1563
49. Goodell, V.; et al., J. Clin. Oncol. 2006 24 762 768
50. Chapman, C.; et al., Ann. Oncol. 2007 18 868 873
51. Disis, M. L.; et al., Cancer Res. 1994 54 16 20
52. Disis, M. L.; et al., Breast Cancer Res. Treat. 2000 62 245 252
53. Regele, S.; et al., Anticancer Res. 2003 23 761 764
54. Green, J. A.; et al., Eur. J. Cancer 1994 30A 580 584
55. Mudenda, B.; et al., Br. J. Cancer 1994 69 1115 1119
56. Gao, R. J.; et al., Breast Cancer Res. Treat. 2005 93 111 115
57. Angelopoulou, K.; et al., Int. J. Cancer 1994 58 480 487
58. Regidor, P. A.; et al., Eur. J. Gynaecol. Oncol. 1996 17 192 199
59. Peyrat, J. P.; et al., Lancet 1995 345 621 622
60. Dalifard, I.; et al., Anticancer Res. 1999 19 5015 5022
61. Kotera, Y.; et al., Cancer Res. 1994 54 2856 2860
62. Bachelot, T.; et al., Br. J. Cancer 2006 94 1066 1070
63. Carter, D.; et al., Clin. Cancer Res. 2003 9 749 754
64. Conroy, S. E. et al., Lancet 1995 345 126
65. Suzuki, H. et al., Clin. Cancer Res. 2005 11 1521 1526
66. Pupa, S. M. et al., Ann. Oncol. 2002 13 483

Example 3

Additional Data on using the Antibody Panel for Breast Cancer Diagnosis

Serum antibody responses to 8 tumor antigens were evaluated in 98 breast cancer patients (Tumor Vaccine Group, Seattle, Wash.; HER2 positive by FISH or IHC) and 98 age- and gender-matched volunteer control donors (Puget Sound Blood Bank, Seattle, Wash.). The female subjects ranged in age from 34-76 (cancer group) and 24-76 (control group), and each group had an average age of 52. The cancer patients had gone through surgery and chemotherapy and have stable disease. Samples were collected at their initial visit and prior to any vaccination treatment.

Tumor cell-based ELISA was used to measure antibody to HER2/neu as described previously. In brief, the SKBR3 cell line was used as a source for HER2/neu protein. 96-well microtiter plates were coated with 520C9, a monoclonal antibody specific to HER2/neu before SKBR3 cell lysate (20 µg/ml) was added to the wells. Plates were washed again and serially diluted patient sera were added to wells. Serum from a patient with known anti-HER2 antibody was used as a positive control and included on each plate. Similarly, a negative control of PBS/BSA buffer was included in each plate.

Indirect ELISA with recombinant protein was used to measure antibodies to p53, CEA, TOPO2α, cyclin B1, IGFBP2, and Cathepsin D. As described previously, microtiter plates were coated with purified recombinant protein from commercial sources, blocked for 1 hour with PBS/BSA, and washed with PBS/Tween. After washing, 50 µl/well of patient sera were added in titration sets. The addition of secondary antibody and plate development was similar to the ELISA for HER2.

Figure 10:
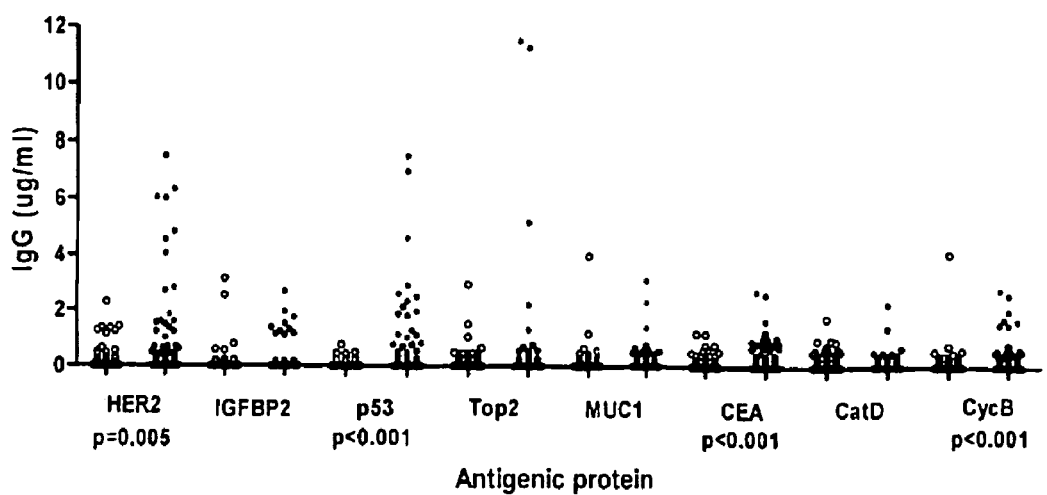
FIG. 10. Breast cancer patients have elevated levels of serum antibodies to HER2, p53, CEA, and Cyclin B1. Shown are the magnitude of antibody responses in 98 breast cancer patients (solid dots) and 98 controls (open circles). Each data point represents the value from an individual patient or control.
Figure 11:
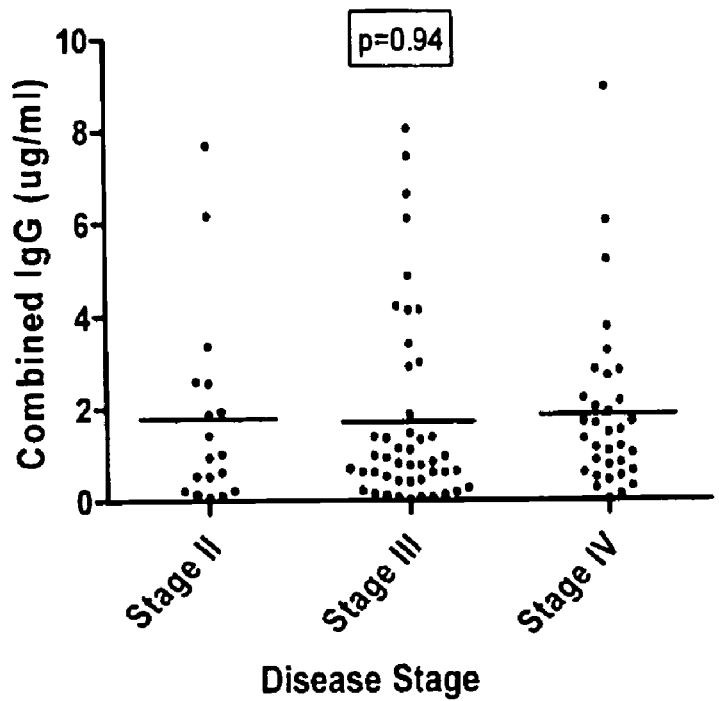
FIG. 11. There is no difference in serum antibody responses between different disease stages. Shown are the combined antibody responses to 4 tumor antigens: HER2, p53, CEA and cycB1.

Breast cancer patients have significantly higher levels of serum antibodies to HER2, p53, CEA, and cyclin B1 (p<0.05) (FIG. 10). Furthermore, there is no statistical difference in the antibody responses between different disease stages, indicating that early stage disease can be as immunogenic as late stage disease (FIG. 11).

Figure 12:
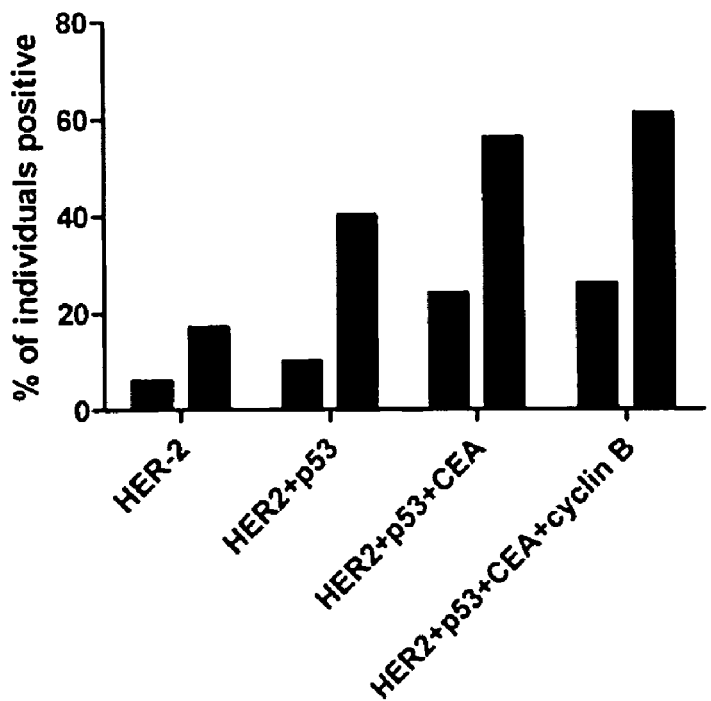
FIG. 12. 61% of the breast cancer patients have antibody responses to at least one of the 4 antigens that induce higher responses in cancer patients than controls. Shown are the positive response rates for a single or combined antigens in breast cancer patients (brown columns) and controls (blue columns).
Figure 13:
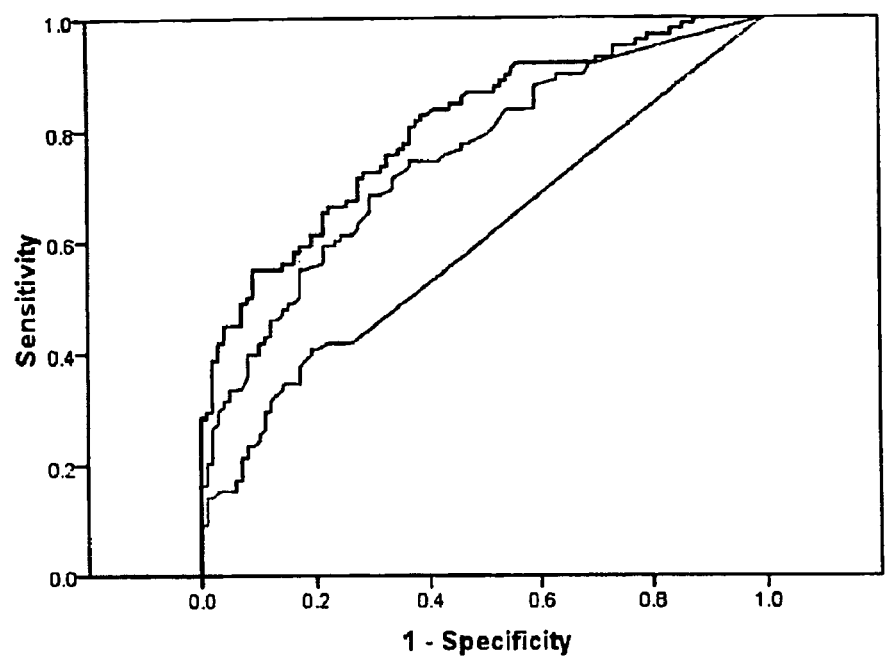
FIG. 13. A combination of serum antibody markers may be useful for disease diagnosis. Shown are ROC curves of assay performance using a single or combined antibody responses. Green line (lowermost): anti-HER2 Ab alone, AUC=0.599; Blue line (middle): sum of 4 antibody responses, AUC=0.748, Black line (uppermost; predicted probability): sum of antibody responses weighted on the coefficient from logistic regression, AUC=0.803.

Although each antibody is only present in a small percentage of cancer patients, usually less than 20%, we have shown that the majority of patients have antibody response to at least one antigen when we tested the serum antibody response to a panel of 4 antigens (FIG. 12). A panel of antigens performs better than single antigen markers in discriminating sera from breast cancer patients vs. control donors. As shown in the receiver operating curve (ROC) analysis in FIG. 13, using a single antibody (anti-HER2), the assay performance has a an area under the curve (AUC) on ROC of 0.599. The AUC increased to 0.748 when the combination of 4 antigens (cycB1+CEA+p53+HER2) was used. The AUC was further increased to 0.803 when a prediction algorithm weighted on the logistic regression coefficient of each antigen was used (FIG. 13).

Example 4

Antibody Panel for Diagnosis and Prognosis of Ovarian Cancer

Figure 14:
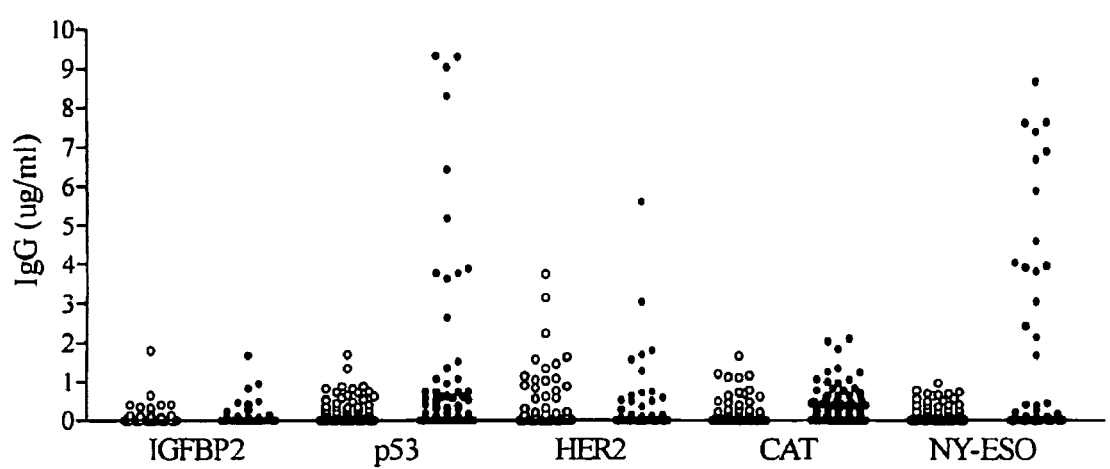
FIG. 14. Antibodies to tumor associated antigens are more frequently detected in sera from ovarian cancer patients than from volunteer healthy donors. (A) The magnitude of antibody response to 5 tumor antigens, IGFBP2, p53, HER2, Cathepsin D, and NY-ESO-1 in ovarian cancer patients (closed circles) and volunteer controls (open circles). Asterisk indicates nine values off the graph.
Figure 15:
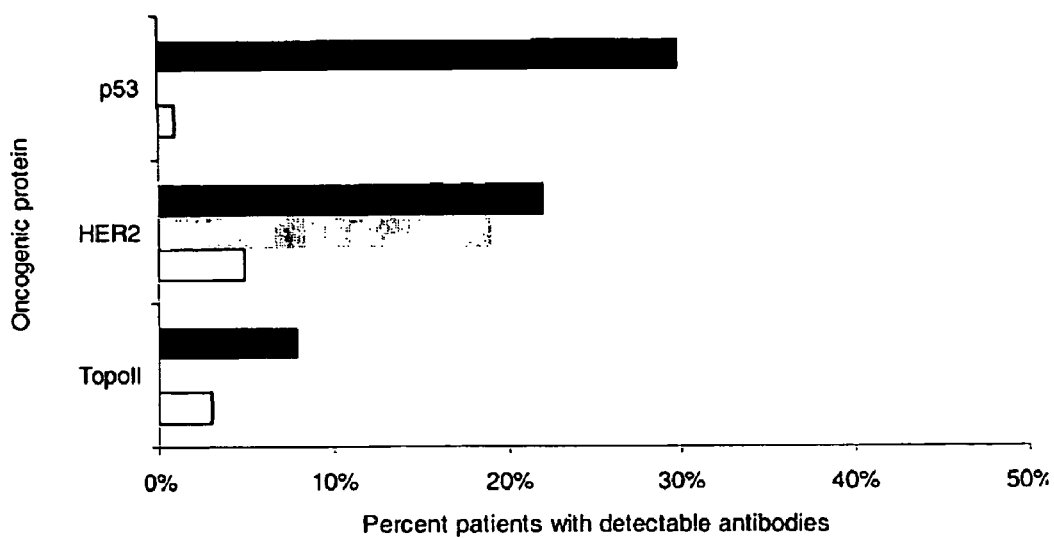
FIG. 15. Early stage ovarian cancer patients also have detectable serum antibody response to tumor antigens. Shown are percentages of patients with detectable antibodies to three tumor antigens in ovarian cancer patients with advanced disease (stage III and IV, black column), limited disease (stage I/II, gray column), and volunteer donors (white column).
Figure 16:
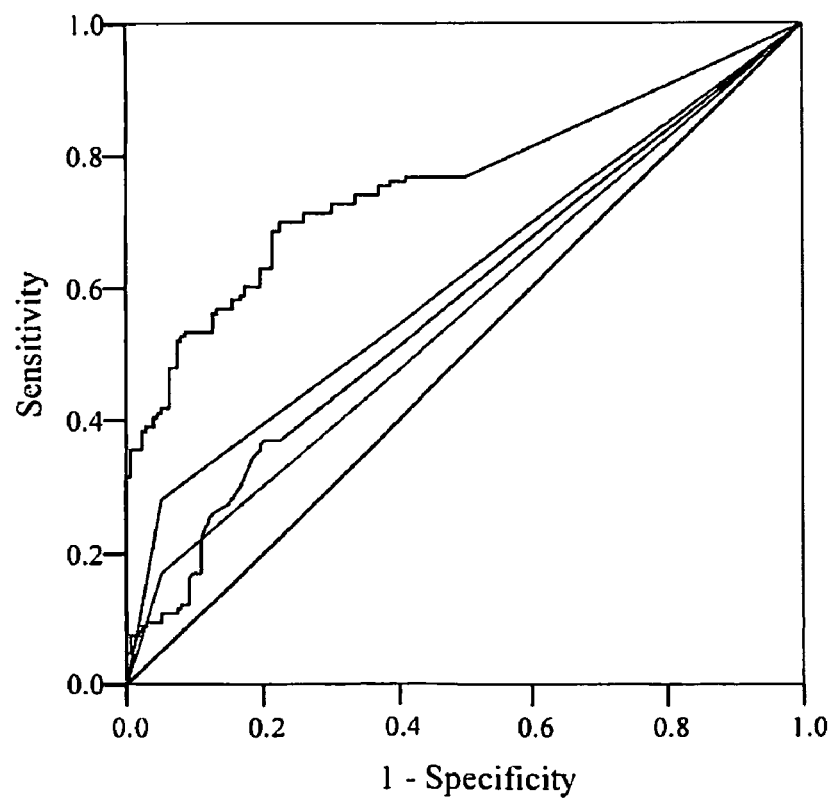
FIG. 16. Serum test based on antibodies to HER2, IGFPB2, p53, and Topo2α may have diagnostic value. Shown is the Receiver Operating Characteristics (ROC) curve of assays examining single or the combination of antibodies. Purple line (uppermost): combination of 4 antigens, AUC=0.762.

There is strong evidence demonstrating that ovarian cancer is immunogenic. Tumor infiltrating lymphocytes found in tumors of ovarian cancer patients have been shown to be associated with a favorable prognosis. A number of serum antibodies that recognize ovarian cancer specific antigens have been identified, including NY-ESO-1, p53, topoisomerase II-alpha (TOPO2α). We have found that ovarian cancer patients have increased serum antibody responses to p53, HER-2/neu, and NY-ESO-1 (FIG. 14). Furthermore, we have found that early stage ovarian cancer patients have serum antibody responses to tumor antigens (FIG. 15). Recent work from our group suggests that multiple antibody markers may be useful in distinguishing ovarian cancer patients from volunteer donors. As shown in FIG. 16, discriminatory power increases as the number of antibodies included in the screening panel is increased. Serum from 149 patients with all stages of ovarian cancer and 200 volunteer controls were assayed using a panel of antibodies to HER-2/neu, TOPO2α, p53, and IGFBP2 and results were used to build ROC curves. Using only the assay for HER-2/neu specific antibodies resulted in an area under the curve (AUC) of 0.560. The AUC increased to 0.578 upon addition of TOPO2α antibodies, and again to 0.614 upon addition of IGFBP2 antibodies to the panel. Increasing the number of antibodies in the panel to 4 by including p53 antibodies and using the predicted probability values obtained through binary logistic regression rather than raw values resulted in an AUC of 0.762 (95% C.I. 0.706-0.817) (FIG. 16).

In addition to the role in diagnosis, we have found that serum antibodies may be useful in prognosis. There is a significant trend toward increased median survival for advanced stage subjects as immunity spreads to a greater number of markers. Median overall survival time for subjects without antibodies to p53, HER2, or TOPO2α was 24 months.

Figure 17:
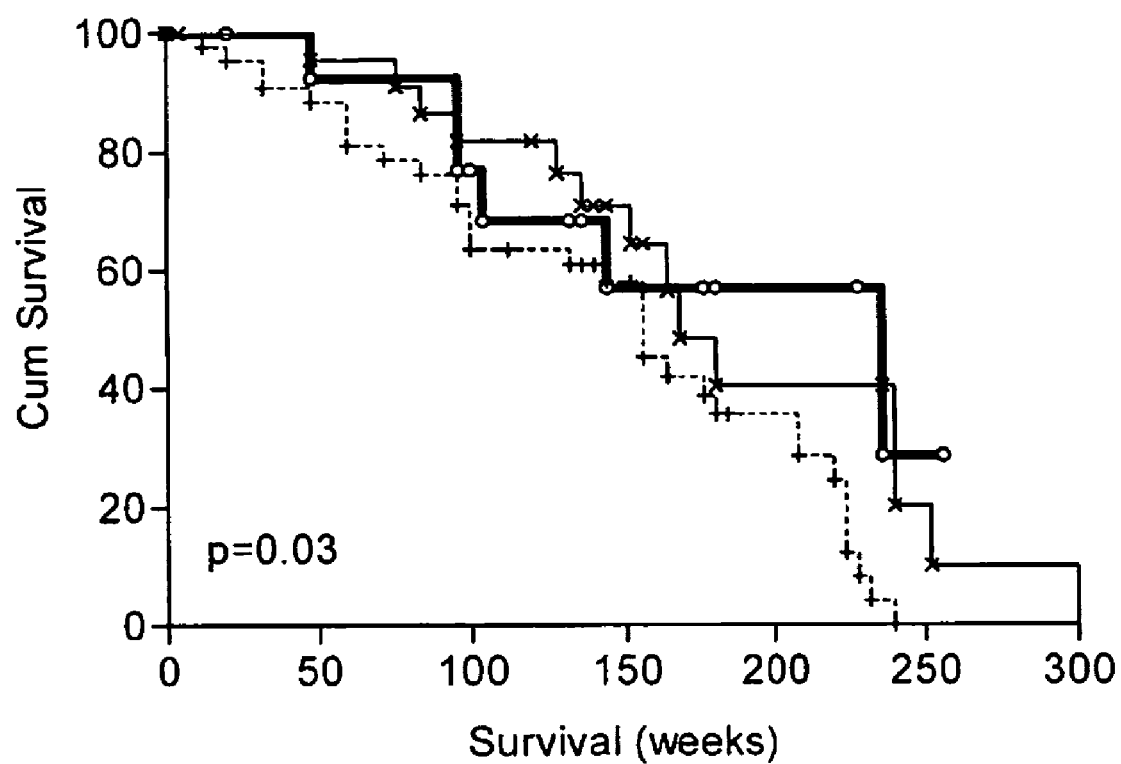
FIG. 17. There is a significant trend toward increased median survival as immunity spreads to a greater number of markers. Median overall survival time is higher in subjects with antibodies to one marker (unbroken line) than in subjects without marker-specific antibodies (dotted line), and highest for subjects with antibodies to two of three markers (dashed line).

Subjects positive for any one of the 3 markers studied had an increase in median overall survival from 24 to 38 months, and subjects positive for any 2 antibodies studied had an increase in overall survival from 38 to 42 months. The linear relationship between number of markers with positive antibody response and median survival time was significant (p=0.03) by the log-rank test for trend (FIG. 17). (Lu H, et al., Serum antibodies specific for tumor antigens in breast cancer may be useful diagnostic biomarkers. Poster presentation at the 2008 Annual Meeting of American Association of Clinical Oncology, Chicago, Ill., USA.)

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for detection of a malignancy associated with breast cancer in a test specimen of bodily fluid, the method comprising:
    (a) contacting the specimen with at least two antigens selected from the group consisting of p53, IGFBP2, Topo2α, cathepsin D, cyclin B, cyclin D1, MUC1, HER-2/neu and CEA;
    (b) incubating the specimen and the antigens for a duration and under conditions that are sufficient for the formation of immunocomplexes;
    (c) detecting the presence or absence of immunocomplex formation between the antigens and antibodies specific for the antigens in the specimen, and
    (d) determining the presence or absence of the malignancy, wherein presence of immunocomplex formation is indicative of malignancy; and
    wherein the at least two antigens comprise p53, cyclin B, HER-2/neu and CEA.

2. The method of claim 1, wherein the at least two antigens further comprise cathepsin D.

3. The method of claim 1, wherein the at least two antigens further comprise IGFBP2, and Topo2α.

4. The method of claim 1, wherein the contacting of step (a) comprises contacting the specimen with cathepsin D, IGFBP2, cyclin B, p53, Topo2α and CEA.

5. The method of claim 1, wherein the contacting of step (a) comprises contacting the specimen with p53, CEA, HER-2/neu, IGFBP2, Topo2α, MUC1, cathepsin D, cyclin B, and cyclin D1.

6. A method for monitoring the effectiveness of breast cancer therapy related to a malignancy associated with breast cancer in a warm-blooded animal, the method comprising the steps of:
    (a) contacting a specimen of bodily fluid obtained from the warm-blooded animal with at least two antigens selected from the group consisting of p53, IGFBP2, Topo2α, cathepsin D, cyclin B, cyclin D1, MUC1, HER-2/neu and CEA;
    (b) incubating the specimen and the antigens for a duration and under conditions that are sufficient for the formation of immunocomplexes;
    (c) detecting the presence or absence of immunocomplex formation between the antigens and antibodies specific for the antigens in the specimen, and
    (d) determining the presence or absence of the malignancy, wherein presence of immunocomplex formation is indicative of malignancy; and
    wherein the at least two antigens comprise p53, cyclin B, HER-2/neu and CEA.

7. The method of claim 6, wherein steps (a)-(c) are repeated following an administration of cancer therapy, and effectiveness of the cancer therapy is determined by comparing results of the detecting of step (c) performed before and after the administration of cancer therapy.

8. The method of claim 1, further comprising comparing the presence of immunocomplex formation in the specimen to the presence of immunocomplex formation in a control specimen from a normal donor, wherein the presence of immunocomplex formation in the test specimen that is at least 2 standard deviations above the mean amount of immunocomplex formation in the control specimen for at least one of the antigens is indicative of malignancy.

* * * * *